(12) United States Patent
Yamada et al.

(10) Patent No.: US 7,690,788 B2
(45) Date of Patent: Apr. 6, 2010

(54) DRIVING CIRCUIT OF ELECTROMECHANICAL TRANSDUCER DEVICE AND RETINA SCANNING DISPLAY DEVICE HAVING THE SAME

(75) Inventors: Shoji Yamada, Nagoya (JP); Haruhisa Takayama, Nagoya (JP)

(73) Assignee: Brother Kogyo Kabushiki Kaisha, Nagoya (JP)

(*) Notice: Subject to any disclaimer, the term of this patent is extended or adjusted under 35 U.S.C. 154(b) by 78 days.

(21) Appl. No.: 12/076,933

(22) Filed: Mar. 25, 2008

(65) Prior Publication Data

US 2008/0180633 A1   Jul. 31, 2008

Related U.S. Application Data

(63) Continuation-in-part of application No. PCT/JP2006/319212, filed on Sep. 27, 2006.

(30) Foreign Application Priority Data

Sep. 29, 2005   (JP)   ............................. 2005-284806

(51) Int. Cl.
*A61B 3/10* (2006.01)
(52) U.S. Cl. ...................... 351/221; 351/220
(58) Field of Classification Search .......... 351/200–246
See application file for complete search history.

(56) References Cited

U.S. PATENT DOCUMENTS

| | | | |
|---|---|---|---|
| 5,130,598 A * | 7/1992 | Verheyen et al. ....... | 310/316.03 |
| 6,276,772 B1 * | 8/2001 | Sakata et al. .................. | 347/10 |
| 6,528,925 B1 * | 3/2003 | Takeuchi et al. ....... | 310/316.03 |

FOREIGN PATENT DOCUMENTS

| | | |
|---|---|---|
| DE | 101 51 421 A1 | 5/2002 |
| DE | 600 27 829 T2 | 12/2006 |
| EP | 1 079 447 A2 | 2/2001 |
| JP | A 2001-60116 | 3/2001 |
| JP | A 2002-159190 | 5/2002 |
| JP | A 2005-41076 | 2/2005 |
| JP | A 2005-181477 | 7/2005 |
| JP | A 4-285479 | 10/2009 |

* cited by examiner

*Primary Examiner*—Mohammed Hasan
(74) *Attorney, Agent, or Firm*—Oliff & Berridge, PLC

(57) ABSTRACT

The present invention provides a drive circuit for driving a capacitive electromechanical transducer device. The capacitive electromechanical transducer device is constituted of two electromechanical transducer parts consisting of a first capacitive electromechanical transducer part and a second capacitive electromechanical transducer part and is operated in response to two-phase sinusoidal signals having mutually opposite phases. The drive circuit includes an inductor which resonates with the first electromechanical transducer part and the second electromechanical transducer part, and a resonance frequency of the resonance circuit is set substantially equal to an operation frequency of the electromechanical transducer device.

18 Claims, 18 Drawing Sheets

Fig.13
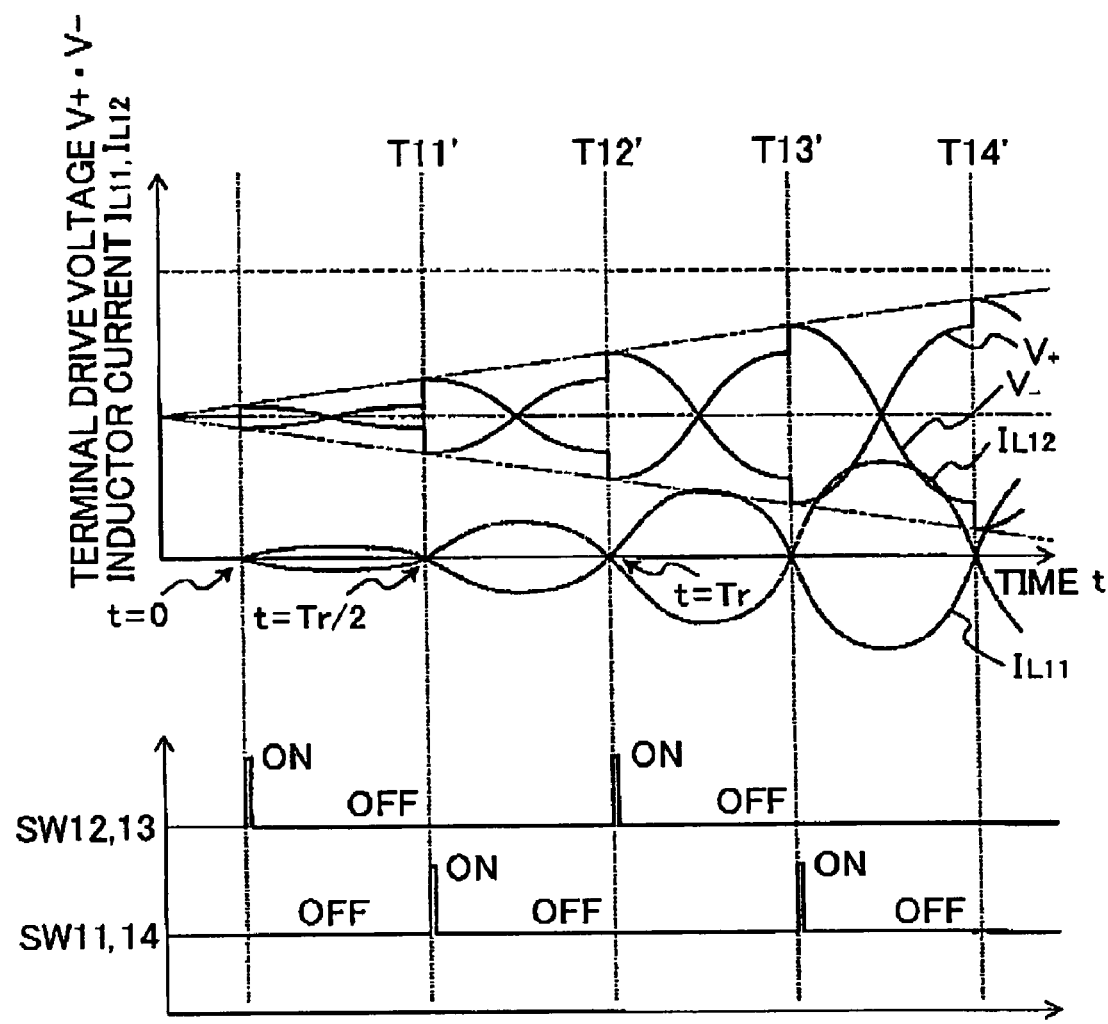
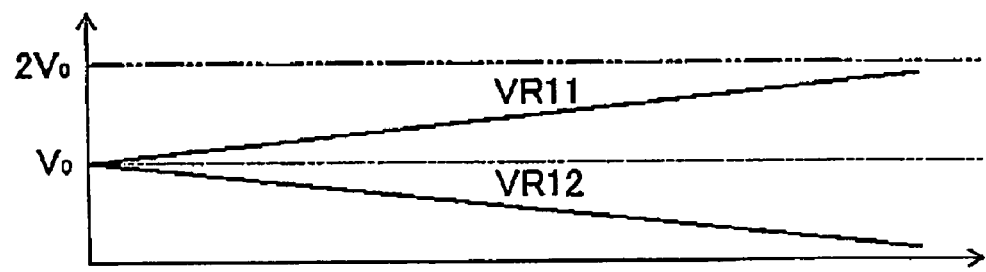

DRIVING CIRCUIT OF ELECTROMECHANICAL TRANSDUCER DEVICE AND RETINA SCANNING DISPLAY DEVICE HAVING THE SAME

CROSS-REFERENCE TO RELATED APPLICATIONS

The present application is a Continuation-in-Part of International Application No. PCT/JP2006/319212 filed Sep. 27, 2006, which claims the benefit of Japanese Patent Application No. 2005-284806 filed Sep. 29, 2005.

BACKGROUND OF THE INVENTION

1. Field of the Invention

The present invention relates to a drive circuit for driving a capacitive electromechanical transducer device and an image display device including the drive circuit, and more particularly to a drive circuit for operating an optical scanning mirror using a capacitive electromechanical transducer device constituted of a plurality of piezoelectric elements or the like and a retina scanning display device (retinal scanning display device) including the drive circuit.

2. Description of the Related Art

Recently, there has been proposed an image display device which allows an optical flux to be incident on a pupil and the incident optical flux to be projected on a retina so that a viewer can observe a virtual image in front of the pupil. That is, there has been proposed a so-called retina scanning device.

This type of retina scanning display device uses an optical flux scanning means for scanning the optical flux in the horizontal direction or in the vertical direction. For example, patent document 1 (JP-A-2005-181477) describes an optical scanner constituted of a capacitive electromechanical transducer device as an optical scanning means.

FIG. 17 shows one example of an optical scanner 200 of a mechanical resonance system constituted of a capacitive electromechanical transducer device. The optical scanner 200 is, for scanning the optical flux direction, configured to oscillate by resonance an oscillatory body 224 which arranges a reflection mirror 220 for reflecting the optical flux and changing the radiation direction of the optical flux therein.

As shown in FIG. 17, the oscillatory body 224 is supported on a fixed frame 216, and includes two piezoelectric elements 250, 252 which are fixed to the oscillatory body 224 and the fixed frame 216 respectively. Here, the piezoelectric elements 250, 252 respectively function as drive sources, and generate torsional oscillations about an oscillation shaft Lr so as to oscillate the reflection mirror 220.

Here, FIG. 18 shows an equivalent circuit of the optical scanner 200 and a drive circuit 270 of the optical scanner 200.

As shown in FIG. 18, the piezoelectric element 250 of the optical scanner 200 can be expressed as a circuit in which a resonance circuit 280 formed by connecting an $L_{M100}$, a $C_{M100}$ and an $R_{M100}$ in series and a capacitor $C_{P100}$ are connected in parallel to each other. In the same manner, the piezoelectric element 252 of the optical scanner 200 can be expressed as a circuit in which a resonance circuit 282 formed by connecting an $L_{M101}$, a $C_{M101}$ and an $R_{M101}$ in series and a capacitor $C_{P101}$ are connected in parallel to each other.

Then, the drive circuit 270 inputs a positive-phase sinusoidal signal $V_+$ ($=Vo\{1+\cos(2\pi ft)\}$) to the piezoelectric element 250 via a transistor Tr100, and inputs a negative-phase sinusoidal signal $V_-$ ($=Vo\{1-\cos(2\pi ft)\}$) to the piezoelectric element 252 via a transistor Tr101.

In this manner, by inputting the two-phase sinusoidal signals having phases different from each other to the piezoelectric elements 250, 252, the driving circuit 270 generates the torsional oscillations in the oscillatory body 224 about the oscillation axis Lr thus oscillating the reflection mirror 220.

SUMMARY OF THE INVENTION

However, in the conventional driving method, the above-mentioned sinusoidal signals are outputted to the piezoelectric elements constituting capacitive loads using linear amplifiers (for example, Tr100, Tr101) and hence, a reactive current attributed to charging/discharging of the capacitive load is generated. The power consumption is increased due to such a reactive power.

With respect to an image display device such as a retina scanning display device, there has been a demand for the enhancement of portability and miniaturization of the display device and hence, it is necessary to suppress the power consumption as small as possible. Accordingly, it is also hardly allowable to ignore the power in the drive circuit for driving the capacitive electromechanical transducer device.

Accordingly, it is an object of the present invention to provide a drive circuit which can suppress the power consumption required for driving a capacitive electromechanical transducer device.

To achieve the above-mentioned object, according to a first aspect of the present invention, there is provided a drive circuit for driving a capacitive electromechanical transducer device operated in response to two-phase sinusoidal signals having phases opposite to each other, wherein the driver circuit includes an inductor forming a resonance circuit having a resonance frequency substantially equal to an operation frequency of the electromechanical transducer device together with the electromechanical transducer device.

Due to such a constitution, it is possible to obviate the power consumption generated by a reactive power attributed to charging/discharging of a capacitive load. Further, a linear amplifier also becomes unnecessary and hence, the drive circuit can be constituted of only a digital circuit and a DC power source.

Further, the drive circuit having the above-mentioned constitution may be applicable to a retina scanning display device.

Due to such a constitution, the retina scanning display device can be driven with low power consumption and hence, the linear amplifier becomes unnecessary whereby the drive circuit can be constituted of only the digital circuit and the DC power source.

BRIEF EXPLANATION OF THE DRAWINGS

FIG. 13 is an explanatory view of a control of a switch in the horizontal scanning drive circuit shown in FIG. 11;

PREFERRED EMBODIMENTS OF THE PRESENT INVENTION

First Embodiment

Hereinafter, a retina scanning display device which includes a drive circuit according to this embodiment for driving a mechanical resonance-system optical scanner constituted of a capacitive electromechanical transducer device is specifically explained in conjunction with drawings.

[Constitution of Retina Scanning Display Device 1]

Figure 1:
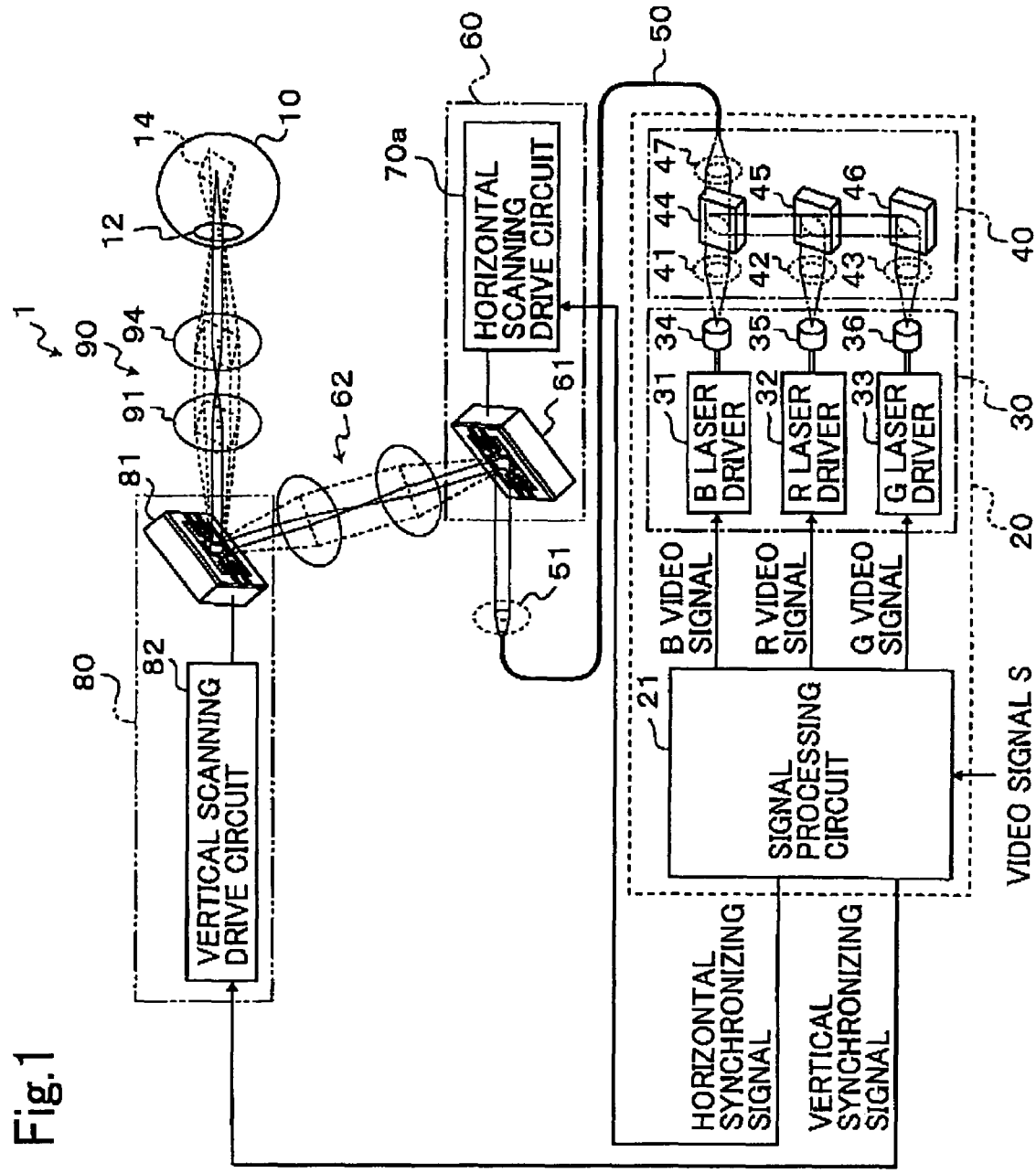
FIG. 1 is a view showing the whole constitution of a retina scanning display device 1 according to an embodiment of the present invention.

First of all, the whole constitution of a retina scanning display device 1 and the manner of operation of the retina scanning display device 1 are explained. The whole constitution of the retina scanning display device 1 of an embodiment of the present invention is shown in FIG. 1. The retina scanning display device 1 is a device of a type which allows a luminous flux to be incident onto a pupil 12 of a viewer who is an user of the retina scanning display device 1 to project an image on the retina 14 so as to allow the viewer to visually recognize a virtual image in front of the pupil 12 of a viewer's eye 10.

The retina scanning display device 1 includes a luminous flux generating part 20 for generating a luminous flux whose intensity is modulated based on a video signal S supplied from the outside. Further, the retina scanning display device 1 includes, between the luminous flux generating part 20 and the viewer's eye 10, a collimation optical system 51 for collimating the luminous flux generated by the luminous flux generating part 20 and radiated from an optical fiber 50, a horizontal scanning part 60 for scanning the luminous flux collimated by the collimation optical system 51 in a horizontal direction for image display, a vertical scanning part 80 for scanning the luminous flux scanned in the horizontal direction using the horizontal scanning part 60 in a vertical direction, a relay optical system 62 formed between the horizontal scanning part 60 and the vertical scanning part 80, and a relay optical system 90 for emitting the luminous flux scanned in the horizontal direction as well as in the vertical direction in this manner (hereinafter, referred to as "scanned luminous flux") onto the pupil 12.

As shown in FIG. 1, the luminous flux generating part 20 includes a signal processing circuit 21 to which a video signal S supplied from the outside is inputted and which generates respective signals or the like constituting components for synthesizing an image based on the video signal S. In the signal processing circuit 21, respective video signals of blue (B), red (R) and green (G) are generated and are outputted. Further, the signal processing circuit 21 outputs a horizontal synchronizing signal used in the horizontal scanning part 60 and a vertical synchronizing signal used in the vertical scanning part 80 respectively.

Further, the luminous flux generating part 20 includes a light source part 30 for forming three video signals (B, R, G) outputted from the signal processing circuit 21 into luminous fluxes respectively, and an optical synthesizing part 40 for generating an arbitrary luminous flux by combining these three luminous fluxes into one luminous flux.

The light source part 30 includes a B laser 34 for generating a blue luminous flux and a B laser driver 31 for driving the B laser 34, an R laser 35 for generating a red luminous flux and an R laser driver 32 for driving the R laser 35, and G laser 36 for generating a green luminous flux and a G laser driver 33 for driving the G laser 36. Here, the respective lasers 34, 35, 36 may be constituted of a semiconductor laser or a solid-state laser with a harmonics generation mechanism, for example.

The optical synthesizing part 40 includes collimation optical systems 41, 42, 43 provided for collimating the luminous fluxes incident from the light source part 30, dichroic mirrors 44, 45, 46 provided for synthesizing the collimated luminous fluxes, and a coupling optical system 47 for guiding a synthesized luminous flux into the optical fiber 50.

The luminous fluxes radiated from the respective lasers 34, 35, 36 are, after respectively being collimated by the collimation optical Systems 41, 42, 43, incident on the dichroic mirrors 44, 45, 46. Thereafter, using these dichroic mirrors 44, 45, 46, the respective luminous fluxes are reflected on the dichroic mirrors 44, 45, 46 or are allowed to pass through the dichroic mirrors 44, 45, 46 selectively with respect to wavelengths thereof.

To be specific, the blue luminous flux radiated from the B laser 34 is, after being collimated by the collimation optical system 41, incident on the dichroic mirror 44. The red luminous flux radiated from the R laser 35 is incident on the dichroic mirror 45 via the collimation optical system 42. The green luminous flux radiated from the G laser 36 is incident on the dichroic mirror 46 via the collimation optical system 43.

The luminous fluxes of three primary colors which are respectively incident on these three dichroic mirrors 44, 45, 46 are reflected on the dichroic mirrors 44, 45, 46 or are allowed to pass through the dichroic mirrors 44, 45, 46 selectively with respect to wavelengths thereof, arrive at the coupling optical system 47 and are converged, and the converged luminous fluxes are outputted to the optical fiber 50.

The horizontal scanning part 60 and the vertical scanning part 80, to bring the luminous fluxes radiated from the optical fiber 50 into a state which allows the luminous fluxes to be projected as an image, scan the luminous fluxes in a horizontal direction as well as in a vertical direction to form the luminous fluxes into scanned luminous fluxes. The horizontal scanning part 60 and the signal processing circuit 21 which includes a constitutional portion for performing horizontal scanning function as a horizontal optical scanner, and the vertical scanning part 80 and the signal processing circuit 21 which includes a constitutional portion for performing vertical scanning function as a vertical optical scanner.

The horizontal scanning part 60 includes a horizontal scanning optical scanner 61 for scanning the luminous fluxes in the horizontal direction as a scanning mirror and a horizontal scanning drive circuit 70a for driving the horizontal scanning optical scanner 61, while the vertical scanning part 80 includes a vertical scanning optical scanner 81 for scanning the luminous flux in the vertical direction as a scanning mirror and a vertical scanning drive circuit 82 for driving the vertical scanning optical scanner 81. Here, the horizontal scanning drive circuit 70a is driven based on a horizontal synchronizing signal outputted from the signal processing circuit 21, while the vertical scanning drive circuit 82 drives the vertical scanning optical scanner 81 based on a vertical synchronizing signal outputted from the signal processing circuit 21, respectively. The horizontal scanning optical scanner 61 and the vertical scanning optical scanner 81 are constituted of the electromechanical transducer device as explained later in detail.

Further, the retina scanning display device 1 includes a relay optical system 62 for relaying the luminous fluxes between the horizontal scanning part 60 and the vertical scanning part 80. Light scanned in the horizontal direction using the horizontal scanning optical scanner 61 passes through the relay optical system 62 and is scanned using the vertical scanning optical scanner 81 in the vertical direction, and is radiated to the relay optical system 90 as the scanned luminous fluxes.

The relay optical system 90 includes sets of lenses 91, 94. The scanned luminous fluxes radiated from the vertical scanning part 80, using the set of lenses 91, have center lines thereof arranged parallel to each other and are respectively converted into converged luminous fluxes. Then, using the set of lenses 94, the converged luminous fluxes are arranged substantially parallel to each other and, at the same time, are converted such that that the center lines of these luminous fluxes are converged on the pupil of the viewer.

[2. Constitution of Horizontal Scanning Optical Scanner 61]

Figure 2:
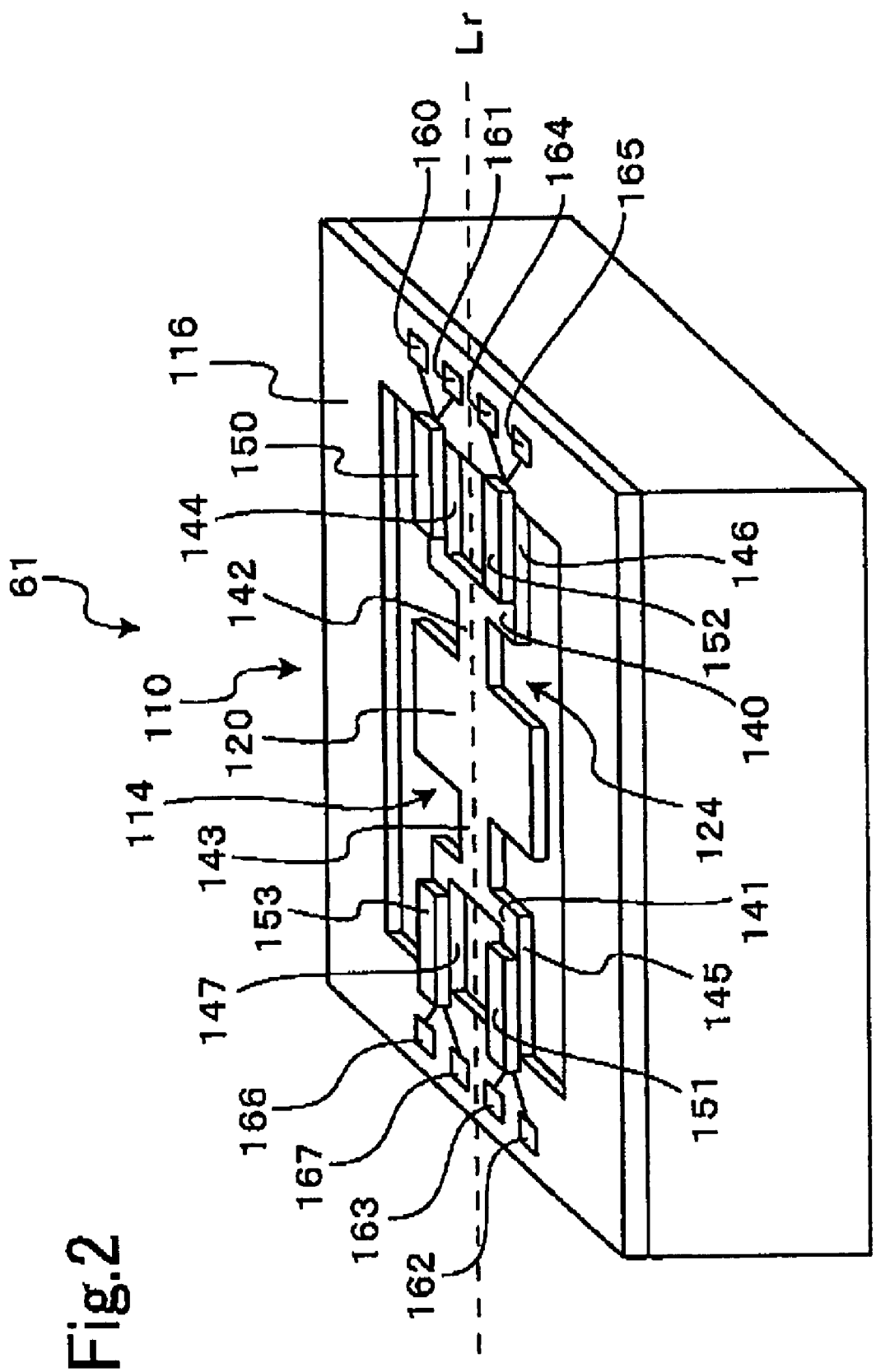
FIG. 2 is a perspective view of a horizontal scanning optical scanner shown in FIG. 1.

Next, the constitution of the optical scanner for scanning the luminous flux in the horizontal direction as described above is specifically explained hereinafter. FIG. 2 is a perspective view showing the horizontal scanning optical scanner 61. Here, since the vertical scanning optical scanner 81 is constituted in the same manner as the horizontal scanning optical scanner 61, the explanation thereof is omitted here.

The horizontal scanning optical scanner 61 is constituted of a capacitive and mechanical resonance-system electromechanical transducer device. For scanning the light spot on the retina 14 in the horizontal direction, an oscillating body 124 which includes a reflection mirror 120 for changing the radiation direction of the luminous flux by reflecting the luminous flux is oscillated by the optical scanning drive circuit 70a. In this embodiment, the oscillating body 124 is allowed to resonate. Due to such resonation of the oscillating body 124, it is possible to oscillate the reflection mirror 120.

As shown in FIG. 2, the horizontal scanning optical scanner 61 includes a through hole 114 and the through hole 114 has an approximately rectangular shape in a plan view. Further, a fixed frame portion 116 is arranged on an outer side of the body portion 110, while the oscillating body 124 which includes the reflection mirror 120 is arranged on an inner side of the body portion 110. Here, the horizontal scanning optical scanner 61 is made of a material having resiliency such as silicon, and piezoelectric element portions 150 to 153 and electrodes and the like described later are formed by a thin film forming method.

The oscillating body 124 is integrally formed of a plurality of constitutional elements. These constitutional elements include the reflection mirror 120, a first beam portion 140 which is constituted of a plate-like resilient member 142 connected to one side of the reflection mirror 120, a plate-like resilient member 144 and a plate-like resilient member 146, and a second beam portion 141 which is constituted of a plate-like resilient member 143 connected to another side of the reflection mirror 120, a plate-like resilient member 145 and a plate-like resilient member 147.

Here, the oscillating body 124 including the reflection mirror 120, the first beam portion 140 and the second beam portion 141 constitutes a movable member which is movable relative to the fixed frame portion 116 fixed to the retina scanning display device 1.

As shown in FIG. 2, the reflection mirror 120 has an approximately rectangular shape and is arranged at an approximately center portion of the body portion 110. The reflection mirror 120 is oscillated about an oscillation axis Lr which extends in the lateral direction in FIG. 2 to change the reflection direction of the light incident on the reflection mirror 120.

On one side of the reflection mirror 120, as described above, two resilient members, that is, the resilient member 144 and the resilient member 146 are branched in parallel to each other from the resilient member 142 with a branching gap wider than a width of the resilient member 142, and two resilient members 144 and 146 are formed in a state that the resilient member 144 and the resilient member 146 are arranged symmetrical with respect to the oscillation axis Lr. In the same manner, on another side of the reflection mirror 120, two resilient members, that is, the resilient member 145 and the resilient member 147 are branched in parallel to each other from the resilient member 143 with a branching gap wider than a width of the resilient member 143, and two resilient members 145 and 147 are formed in a state that the resilient member 145 and the resilient member 147 are arranged symmetrical with respect to the oscillation axis Lr. Further, the first beam portion 140 and the second beam portion 141 are arranged at positions which are symmetrical with respect to the reflection mirror 120.

Further, a first piezoelectric element 150 and a second piezoelectric element 152 are respectively fixedly secured to one-side surfaces of the resilient member 144 and the resilient member 146 which belong to the first beam portion 140. The first piezoelectric element 150 and the second piezoelectric element 152 respectively have one ends thereof fixedly secured to the fixed frame portion 116 as fixed ends, and another ends thereof formed as free ends which are not fixedly secured to the fixed frame portion 116. Here, the first piezoelectric element 150 corresponds to a first electromechanical transducer part, while the second piezoelectric element 152 corresponds to a second electromechanical transducer part.

The first piezoelectric element 150 and the second piezoelectric element 152 respectively have the same structure in which a piezoelectric body is sandwiched by an upper electrode and a lower electrode in the direction perpendicular to fixed surfaces of the first piezoelectric element 150 and the second piezoelectric element 152.

Further, the upper electrode and the lower electrode of the first piezoelectric element 150 are respectively connected to a driving terminal 160 and a driving terminal 161 mounted on the fixed frame body 116, and the upper electrode and the lower electrode of the second piezoelectric element 152 are respectively connected to a driving terminal 164 and a driving terminal 165 mounted on the fixed frame body 116.

Further, in the same manner as the constitution of the first beam portion 140, a third piezoelectric element 151 and a fourth piezoelectric element 153 are respectively fixedly secured to one-side surfaces of the resilient member 145 and the resilient member 147 belonging to the second beam portion 141. Here, the upper electrode and the lower electrode of the third piezoelectric element 151 are respectively connected to a driving terminal 162 and a driving terminal 163 mounted on the fixed frame body 116, and the upper electrode and the lower electrode of the fourth piezoelectric element 153 are respectively connected to a driving terminal 166 and a driving terminal 167 mounted on the fixed frame body 116.

Here, in this embodiment, the explanation is made with respect to the case where the first and second electromechanical transducer parts are used as the first and second piezoelectric elements 150, 152. However, the constitution is not limited to such a case and any part capable of performing capacitive electromechanical transducer can be used as the first and second electromechanical transducer parts.

In the horizontal scanning optical scanner 61 having such a constitution, when a voltage is applied between the upper electrode and the lower electrode of the first piezoelectric element 150, the first piezoelectric element 150 extends or shrinks not only in the direction of voltage application but also in the direction orthogonal to the direction of voltage application. In this manner, the first piezoelectric element 150 extends or shrinks and, at the same time, the bottom surface of the first piezoelectric element 150 is fixed to the resilient body 144 and hence, the first piezoelectric element 150 and the resilient body 144 are bent upwardly or downwardly. Further, in the same manner as the second piezoelectric element 152 and the resilient body 146, when a voltage is applied between the upper electrode and lower electrode of the second piezoelectric element 152, the second piezoelectric element 152 and the resilient body 146 are also resiliently deformed and are bent upwardly or downwardly. Here, the upward bending or the downward bending of the piezoelectric element and the resilient member is controlled based on whether a voltage which is applied between the electrodes assumes a positive polarity or a negative polarity.

Bending of the resilient members 144, 146 due to resilient deformation generates the rotation of the resilient member 142 about the oscillating axis Lr constituting a center axis. Due to this rotation of the resilient member 142, the reflection mirror 120 is rotated about the oscillation axis Lr.

Accordingly, by applying AC voltages having phases opposite to each other between the upper electrode and the lower electrode of the first piezoelectric element 150 and between the upper electrode and the lower electrode of the second piezoelectric element 152, the free ends of the first piezoelectric element 150 and the second piezoelectric element are resiliently deformed and bent such that the free ends of the first piezoelectric element 150 and the second piezoelectric element are displaced in the directions opposite to each other, and the free ends of the first piezoelectric element 150 and the second piezoelectric element repeat upper and lower bending oscillations at a frequency of the AC voltage. The bending oscillations are converted into a rotational movement about the oscillation axis Lr constituting the center axis by way of the first beam portion 140 and hence, the reflection mirror 120 is rotated about the oscillation axis Lr.

Further, the second beam portion 141 is positioned on another side of the reflection mirror 120 as described above and is formed symmetrically with the first beam portion 140 with respect to the oscillation axis Lr, and the rotational oscillations generated by the first beam portion 140 are transmitted to the second beam portion 141 by way of the reflection mirror 120. As a result, the displacements similar to the displacements of the second beam portion are generated. That is, about the oscillation axis Lr constituting the center axis, the resilient member 143 is resiliently deformed and is rotationally oscillated in the approximately same manner as the resilient member 142, and the resilient member 145 is resiliently deformed and generates the bending oscillations in the approximately same manner as the resilient member 146, and the resilient member 147 is resiliently deformed and generates the bending oscillations in the approximately same manner as the resilient member 144.

Here, a third piezoelectric element 151 is fixedly secured to the resilient member 145 of the second beam portion 141. When such bending oscillations as described above are generated in the resilient member 145, the bending oscillations make the third piezoelectric element 151 extend or shrink and are converted into a voltage and a voltage signal corresponding to a torsional quantity of the second resilient member is outputted from the output terminals 162, 163. Further, in the same manner, a fourth piezoelectric element 153 is fixedly secured to the resilient member 147 of the second beam portion 141. When such bending oscillations as described above are generated in the resilient member 147, the bending oscillations are converted into a voltage by the fourth piezoelectric element 153 and a voltage signal corresponding to a torsional quantity of the second resilient member is outputted from the output terminals 166, 167.

[3. Constitution of Horizontal Scanning Drive Circuit 70a]

Figure 3:
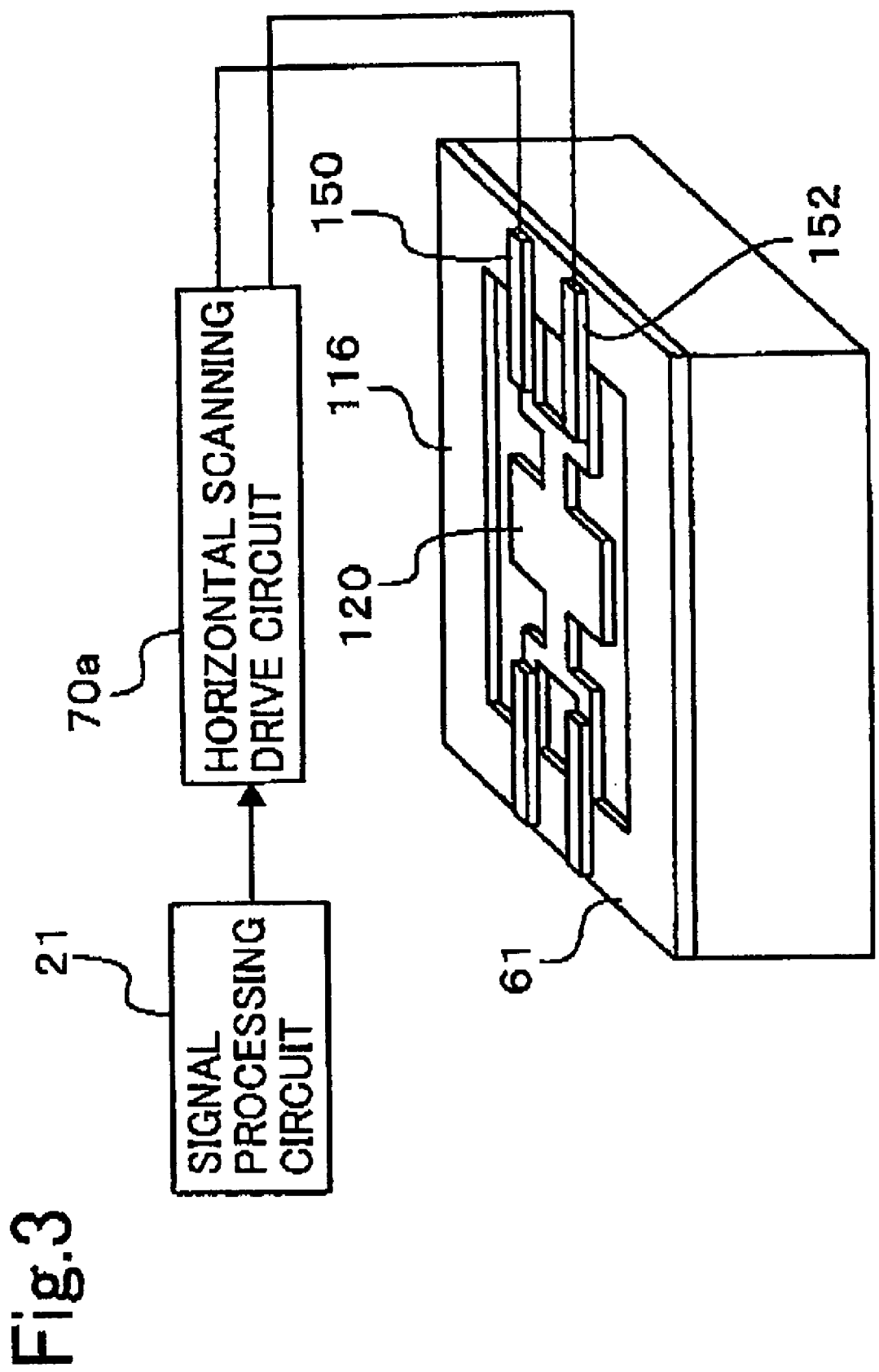
FIG. 3 is a view showing the connection between the horizontal scanning optical scanner and a horizontal scanning drive circuit in the first embodiment.

Next, the horizontal scanning drive circuit 70a for driving the optical scanner is specifically explained hereinafter. FIG. 3 is a view showing the connection between the horizontal scanning optical scanner 61 and the horizontal scanning drive circuit 70a, and FIG. 4 is a view showing the constitution of the horizontal scanning drive circuit 70a.

As shown in FIG. 3, the horizontal scanning drive circuit 70a is connected to the horizontal scanning optical scanner 61. Here, the horizontal scanning drive circuit 70a is operated so that a voltage level of the driving terminal 160 connected to the first piezoelectric element 150 and a voltage level of the driving terminal 164 connected to the second piezoelectric element 152 respectively assume sinusoidal voltages. Further, the driving terminal 161 connected to the first piezoelectric element 150 and the driving terminal 165 connected to the second piezoelectric element 152 are connected to a ground (earthed) by way of the horizontal scanning drive circuit 70a.

Figure 4:
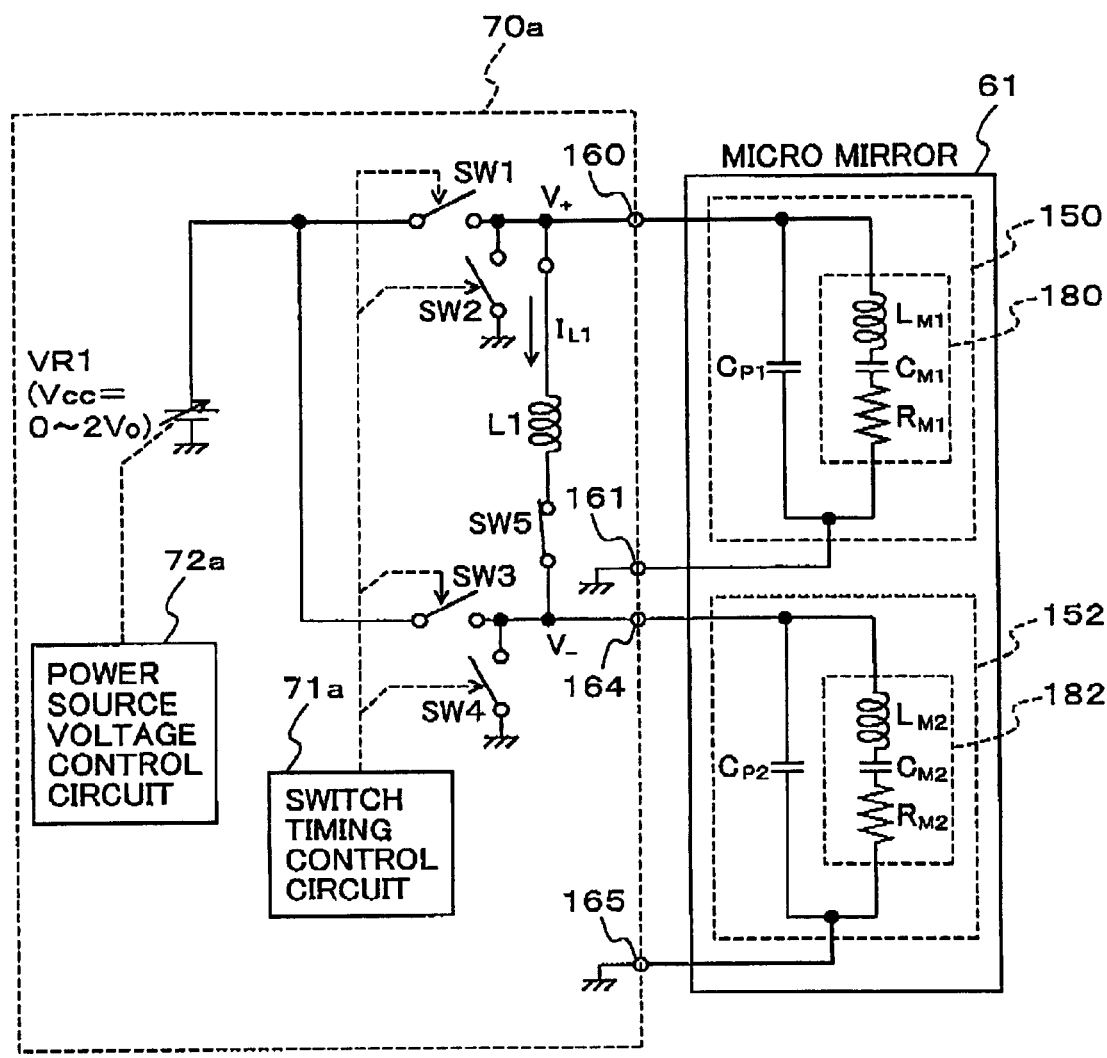
FIG. 4 is a view showing the constitution of the horizontal scanning optical scanner and the horizontal scanning drive circuit in the first embodiment.

In the horizontal scanning drive circuit 70a, as shown in FIG. 4, a switch SW5 and a coil L1 constituting an inductor are connected in series between the driving terminal 160 connected to the first piezoelectric element 150 and the driving terminal 164 connected to the second piezoelectric element 152. By bringing the switch SW5 into a short-circuited state, the driving terminal 160 and the driving terminal 164 are connected via the coil L1.

Here, an equivalent circuit of the first piezoelectric element 150 is, as shown in FIG. 4, expressed as a parallel circuit consisting of an LCR resonance circuit 180 and a capacitor $C_{P1}$, while an equivalent circuit of the second piezoelectric element 152 is, as shown in FIG. 4, expressed as a parallel circuit consisting of an LCR resonance circuit 182 and a capacitor $C_{P2}$. In this embodiment, admittances of the LCR resonance circuits 180, 182 are, compared to admittances of the capacitors $C_{P1}$, $C_{P2}$, small to an extent that the admittances of the LCR resonance circuits 180, 182 can be ignored and hence, the first piezoelectric element 150 can be regarded as a capacitive load formed of the capacitor $C_{P1}$ (hereinafter, referred to as 'first capacitive load'), and the second piezoelectric element 152 can be regarded as a capacitive load formed of the capacitor $C_{P2}$ (hereinafter, referred to as 'second capacitive load'). Here, the capacitor $C_{P1}$ and the capacitor $C_{P2}$ have the same capacitance value $C_P$, the capacitor $C_{M1}$ and the capacitor $C_{M2}$ have the same capacitance value $C_M$, and the coil $L_{M1}$ and the coil $L_{M2}$ have the same inductor value $L_M$.

Here, the resonance circuit is constituted of the first capacitive load, the second capacitive load and the coil L1. A constant of the coil L1 is determined so that the resonance frequency of the resonance circuit becomes substantially equal to the operation frequency of the horizontal scanning optical scanner 61. As described above, the horizontal scanning optical scanner 61 is the electromechanical transducer device which includes the mechanical resonance system and hence, the resonance point becomes the operation frequency of the horizontal scanning optical scanner 61.

Here, the operation frequency of the horizontal scanning optical scanner 61 f1 expressed as follows.

$$f1 = (2\pi)^{-1}(L_M \times C_M)^{-0.5} \quad (1)$$

Further, the resonance frequency of the resonance circuit f2 is expressed as follows.

$$f2 = 1/Tr = (2\pi)^{-1}(L1 \times C_{P1} \times C_{P2}/(C_{P1}+C_{P2}))^{-0.5} \quad (2)$$

Accordingly, the constant of the coil L1 is set such that the relationship $f1 \cong f2$ is established.

The driving terminal 160 of the first piezoelectric element 150 is connected to one end of a switch SW1 and one end of a switch SW2. Further, another end of the switch SW1 is connected to a variable voltage source VR1, while another end of the switch SW2 is connected to the ground. Here, when the switch SW1 is brought into a short-circuited state, the driving terminal 160 is connected to the variable voltage source VR1, while when the switch SW2 is brought into a short-circuited state, the driving terminal 160 is connected to the ground.

In the same manner, the driving terminal 164 of the second piezoelectric element 152 is connected to one end of a switch SW3 and one end of a switch SW4. Further, another end of the switch SW3 is connected to a variable voltage source VR1, while another end of the switch SW4 is connected to the ground. Here, when the switch SW3 is brought into a short-circuited state, the driving terminal 164 is connected to a variable voltage source VR1, while when the switch SW4 is brought into a short-circuited state, the driving terminal 164 is connected to the ground.

The switches SW1 to SW5 are operated by a switching timing control circuit 71a so that short-circuiting and opening of the switches are controlled. Here, the switches SW1 to SW5 are respectively constituted of a MOS-FET or the like. Further, the control circuit is constituted of the variable voltage source VR1, the switches SW1 to SW5 and the switch timing control circuit 71a.

A power source voltage control circuit 72a controls the variable voltage source VR1 to change an output voltage level of the variable voltage source VR1. That is, due to an operation of the power source voltage control circuit 72a, an output level of the variable voltage source VR1 is changed from 0V to 2Vo(V).

Figure 5:
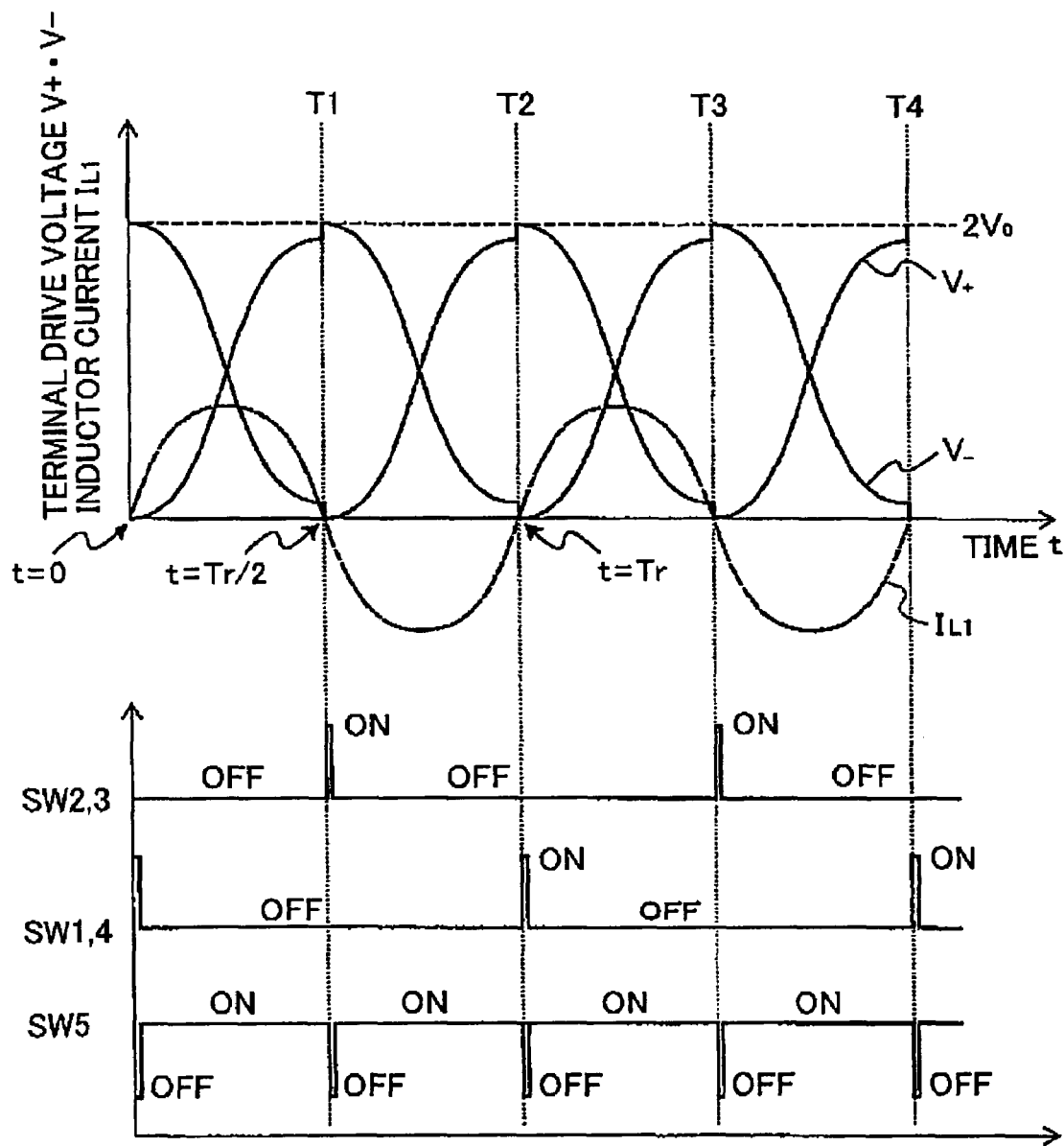
FIG. 5 is an explanatory view of a control of a switch in the horizontal scanning drive circuit shown in FIG. 4.
Figure 6:
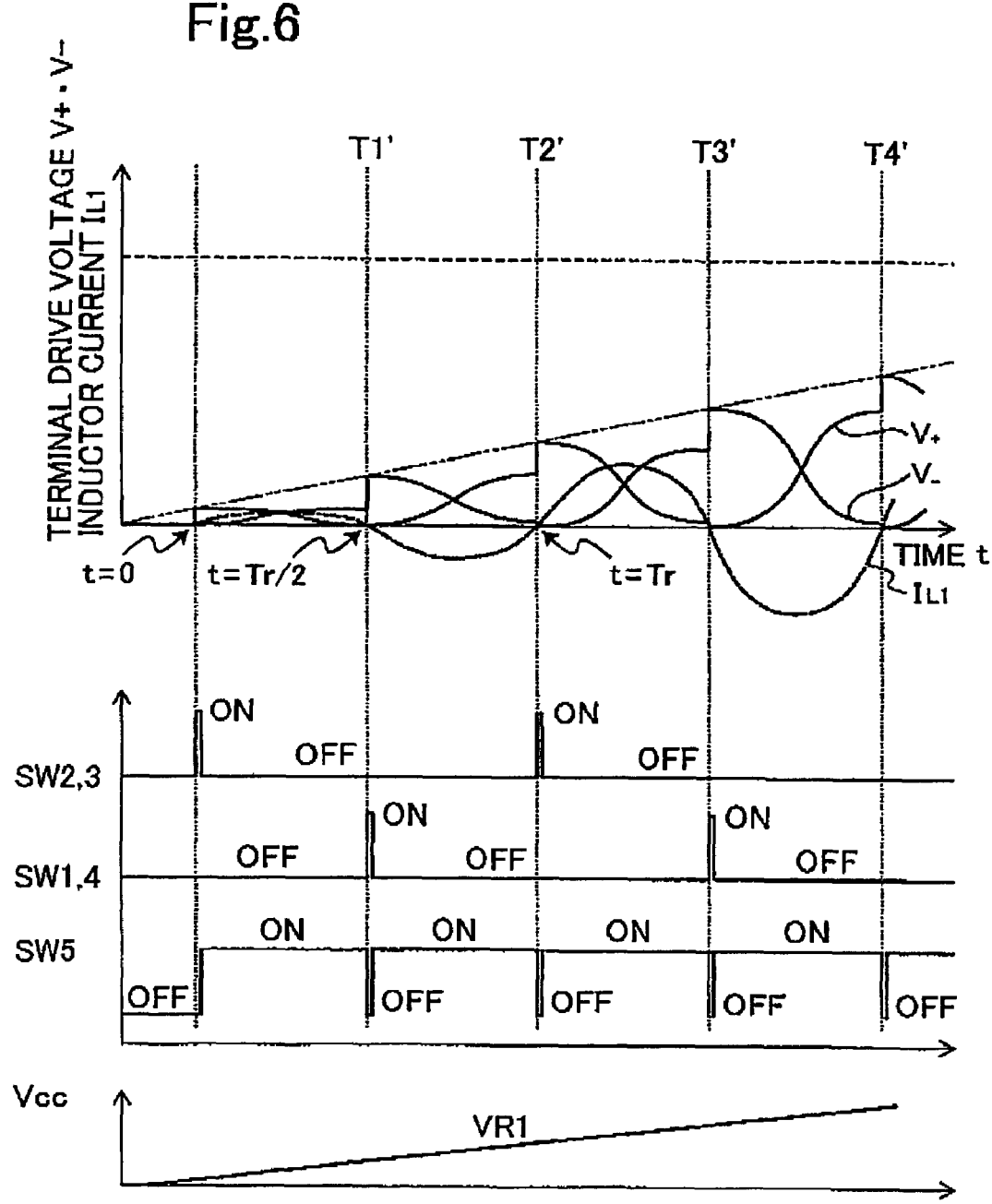
FIG. 6 is an explanatory view of a control of a switch in the horizontal scanning drive circuit shown in FIG. 4.

The operation of the horizontal scanning drive circuit 70a constituted in the above-mentioned manner is specifically explained in conjunction with FIG. 5 and FIG. 6. FIG. 5 and FIG. 6 are views for explaining output signal waveforms in the horizontal scanning drive circuit 70a and control timings of switches SW1 to SW5 by the switch timing control circuit 71a.

As shown in FIG. 5, first of all, by the switch timing control circuit 71a, the switch SW5 is brought into a open-circuited state and the switches SW1 and SW4 are brought into a short-circuited state for a predetermined period (t=0 in FIG. 5). Accordingly, the driving terminal 160 is connected to the variable voltage source VR1 and hence, a charge is charged to the capacitor $C_{P1}$. Further, the driving terminal 164 is connected to GND and hence, the charge of the capacitor $C_{P2}$ is discharged. As a result, the voltage of the capacitor $C_{P1}$ becomes 2Vo(V), while the voltage of the capacitor $C_{P2}$ becomes 0(V). Here, an output voltage Vcc of the variable voltage source VR1 is controlled to become 2Vo(V). That is, the variable voltage source VR1 is operated as a constant voltage source.

Thereafter, the charge charged to the capacitor $C_{P1}$ passes through the coil L1 and is charged to the capacitor $C_{P2}$ (0<t<T1). Accordingly, the voltage levels of the driving terminal 160 and the driving terminal 164 start changing as sinusoidal voltages.

Here, due to the power consumption corresponding to a Q value of the resonance circuit (attributed to the loss of resistance held by the capacitors or the coils), as shown in FIG. 5, amplitude levels of the sinusoidal voltages which change as voltages of the driving terminal 160 and the driving terminal 164 are attenuated and hence, the voltage level of the driving terminal 160 does not arrive at 0(V), while the voltage level of the driving terminal 164 does not arrive at 2Vo(V).

Accordingly, when the voltage level of the sinusoidal voltage which changes as the voltage of the driving terminal 160 from a point of time that the switches SW1 and SW4 are brought into a short-circuited state for the predetermined period assumes a minimum value (or when the voltage level of the sinusoidal voltage which changes as the voltage of the driving terminal 164 from a point of time that the switches SW1 and SW4 are brought into a short-circuited state for the predetermined period assumes a maximum value), that is, after half cycles of the first and second resonance circuits (Tr(Trace ave-length)/2), the switch timing control circuit 71a controls the switches SW2 and SW3 so as to bring these switches SW2 and SW3 into a short-circuited state for a predetermined period (t=T1). Here, the maximum value of the voltage level of the sinusoidal voltage may be an approximately maximum value, while the minimum value of the voltage level of the sinusoidal voltage may be an approximately minimum value.

In this manner, by bringing the switches SW2 and SW3 into a short-circuited state for the predetermined period, it is possible to change the voltage level of the driving terminal 160 from the minimum value to 0(V) and the voltage level of the driving terminal 164 from the maximum value to 2Vo(V) and hence, by charging or discharging a slight amount of charge, it is possible to correct the attenuation of the sinusoidal voltages which change as the voltages of the driving terminal 160 and the driving terminal 164.

In the same manner, hereinafter, the switch timing control circuit 71a, for every first and second half cycles (Tr/2), alternately bring the switches SW1 and SW4 and the switches SW2 and SW3 into a short-circuited state for predetermined periods (t=T2, T3, T4) and hence, the attenuation of the sinusoidal voltages which change as the voltages of the driving terminal 160 and the driving terminal 164 is corrected.

Here, in this embodiment, to facilitate the explanation, the switches SW1 and SW4 and the switches SW2 and SW3 are alternatively brought into a short-circuited state for the predetermined periods for every first and second half cycles (Tr/2) of the resonance circuits. However, when the attenuation of the sinusoidal voltage is small since the Q value of the resonance circuit is large, a control of the switches SW1 to SW4 may be performed in accordance with the attenuation of the sinusoidal voltages form, for example, every 10 cycles or every 20 cycles of the resonance circuit.

In the horizontal scanning drive circuit 70*a*, the main factor of the loss is an inductor loss. Assuming the Q value of $C_P L1$ resonance circuit as Q1, the power consumption P2 of the horizontal scanning drive circuit 70*a* can be expressed as follows.

$$P2=\{2\times(2\pi f2\times C_P\times Vo^2)\}/Q1 \qquad (3)$$

Here, assuming that the resonance frequency as f2=30 kHz, the capacitive value as $C_P$=1 nF, the voltage as Vo=15V and the Q value as Q1=50, the power consumption P2 is expressed as: P2=1.70 mW.

Figure 18:
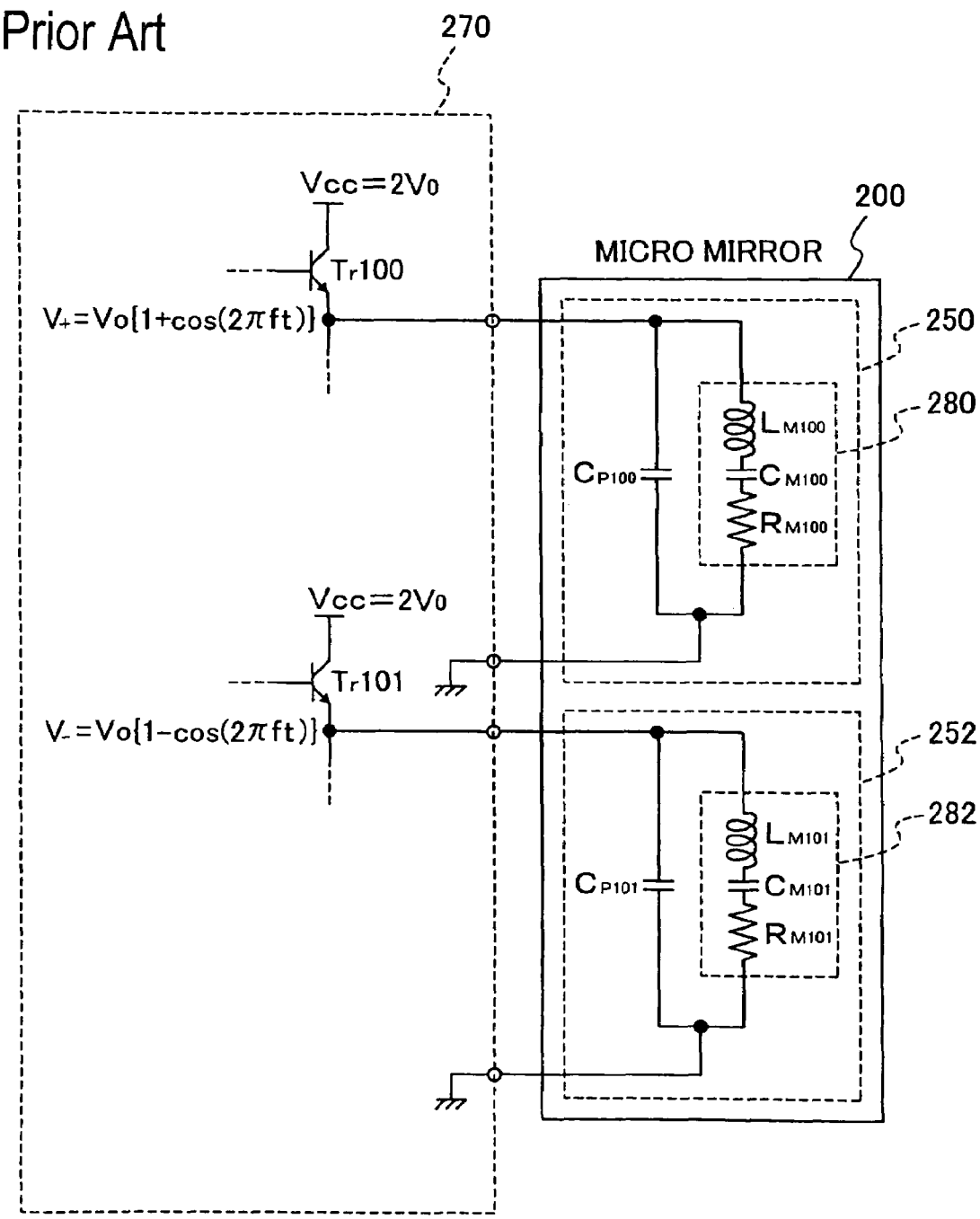
FIG. 18 is a view showing the constitution of the horizontal scanning optical scanner and the horizontal scanning drive circuit of the prior art.

On the other hand, the power consumption P1 in the conventional constitution shown in FIG. 18 can be expressed as follows. Here, the capacitive values of $C_{P100}$ and $C_{P101}$ are assumed as $C_P$.

$$P1=8\times f1\times C_P\times Vo^2 \qquad (4)$$

Here, assuming the operation frequency as f1=30 kHz, the capacitive value $C_P$=1 nF and the voltage as Vo=15V, the power consumption P2 is expressed as P2=5.4 mW.

In this manner, according to this embodiment, it is possible to reduce the power consumption brought about by charging/discharging of the capacitive load. Furthermore, a linear amplifier becomes unnecessary and hence, the horizontal scanning drive circuit 70*a* can be constituted of only a digital circuit and a DC voltage source.

Further, in the horizontal scanning drive circuit 70*a*, at the time of starting the horizontal scanning optical scanner 61, as shown in FIG. 6, it is possible to elevate the output voltage Vcc of the variable voltage source VR1 to a specific value 2Vo(V) by gradually elevating the voltage level. Accordingly, it is possible to suppress electric currents which flow in the first piezoelectric element iso and the second piezoelectric element 152. That is, it is possible to perform gradual charging/discharging of charge to/from the capacitors $C_{P1}$, $C_{P2}$ and, as a result, it is possible to suppress the generation of noises or the like. Further, it is possible to prevent a malfunction of the horizontal scanning optical scanner 61 caused by an overcurrent.

Figure 7:
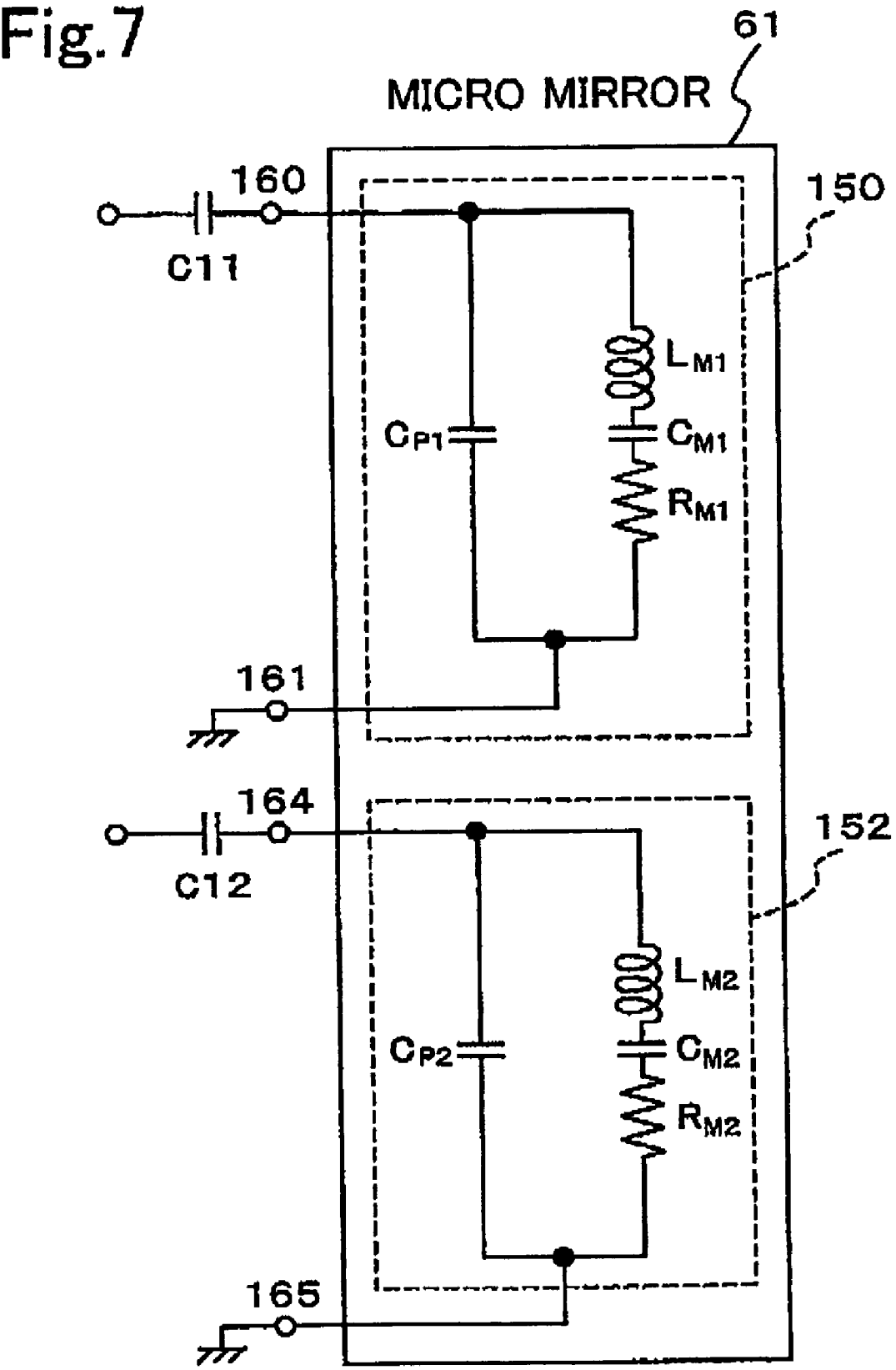
FIG. 7 is an explanatory view of correction capacitors which are connected in series.

Further, in the horizontal scanning drive circuit 70*a*, as shown in FIG. 7, by respectively mounting a correction capacitor C11 in series with the capacitor $C_{P1}$ and a correction capacitor C12 in series with the capacitor $C_{P2}$, when the capacitive values of $C_{P1}$ and $C_{P2}$ differ from each other, it is possible to correct the difference between the capacitive values. Further, it is possible to select an inductor value which can minimize the loss without changing the resonance frequency.

Figure 8:
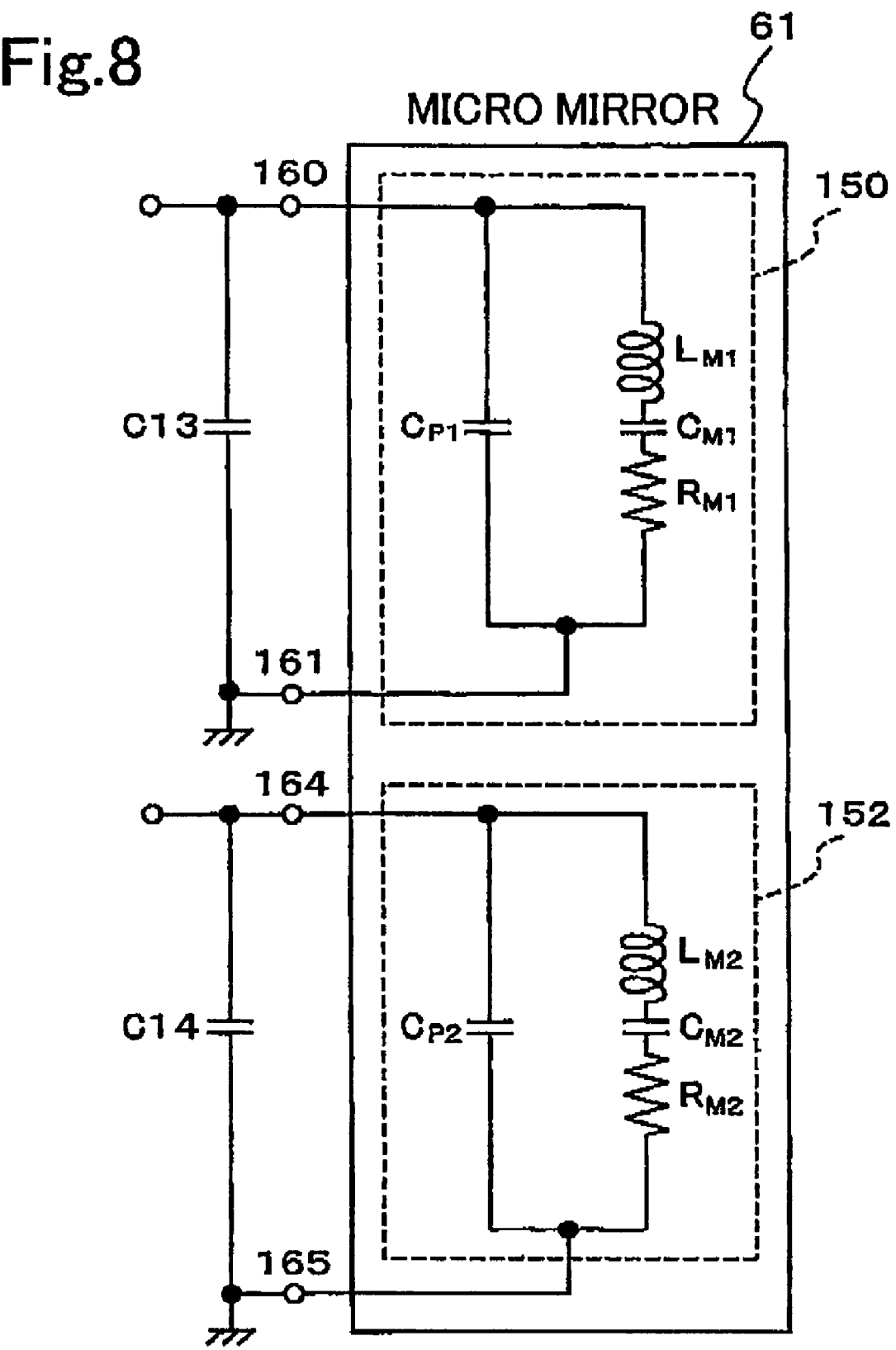
FIG. 8 is an explanatory view of correction capacitors which are connected in parallel.

Further, in the horizontal scanning drive circuit 70*a*, as shown in FIG. 8, by respectively mounting a correction capacitor C13 in parallel to the capacitor $C_{P1}$ and a correction capacitor C14 in parallel to the capacitor $C_{P2}$, it is also possible to obtain the same advantageous effects described above.

Here, the horizontal scanning drive circuit 70*a* is configured to alternately bring the switches SW1 and SW4 and the switches SW2 and SW3 into a short-circuit state for a predetermined period for every half cycle (Tr/2) of the resonance circuit. These timings for controlling the switches are preliminarily set in the switch timing control circuit 71*a* and hence, the switches SW1 to SW4 are controlled at the timings set in this manner.

The control of the switches SW1 to SW4 may be also performed at timings based on a displacement state of the horizontal scanning optical scanner 61. Hereinafter, the constitution which performs the control of the switches SW1 to SW5 at the timings based on the displacement state of the horizontal scanning optical scanner 61 is explained.

Figure 9:
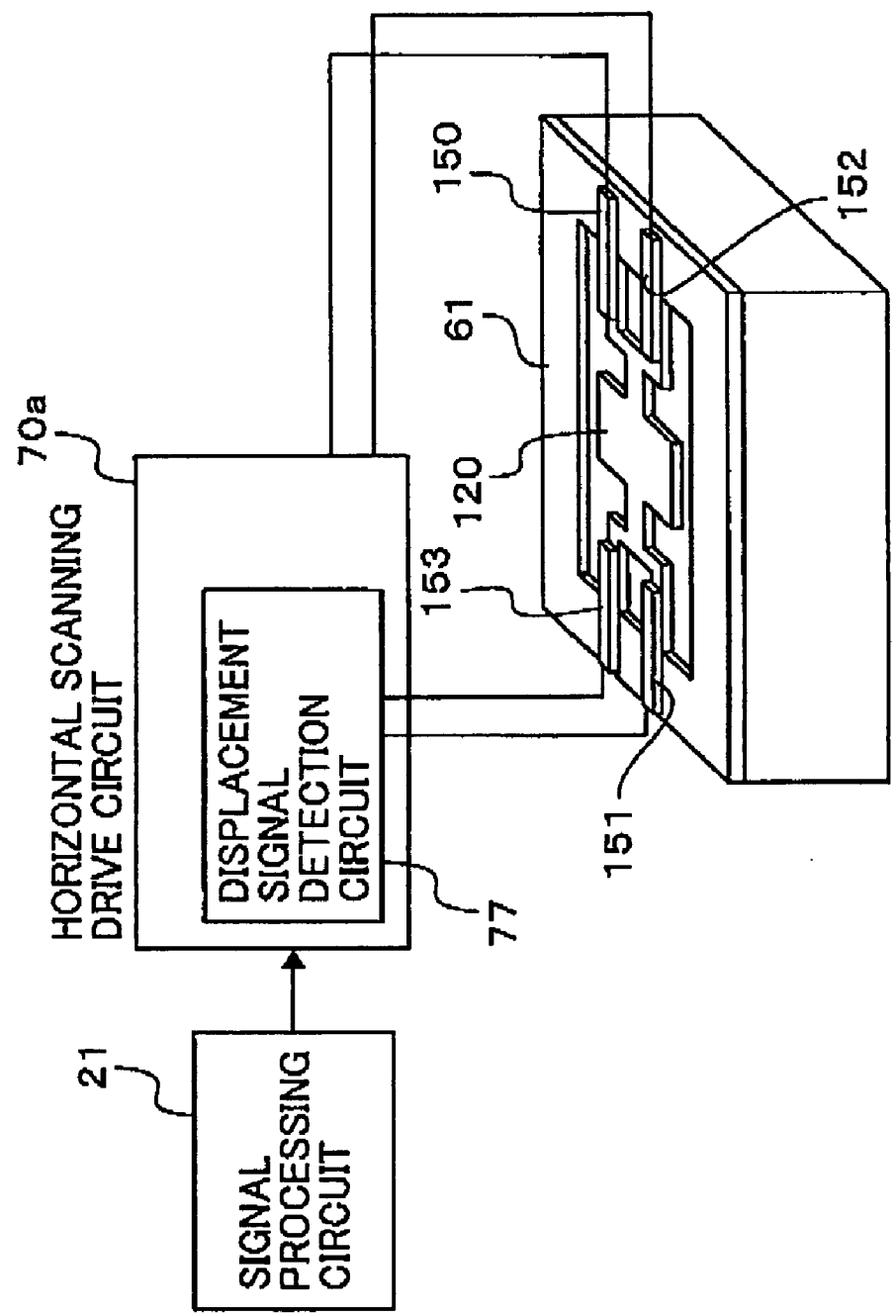
FIG. 9 is a view showing the connection between the horizontal scanning optical scanner and another horizontal scanning drive circuit in the first embodiment.
Figure 10:
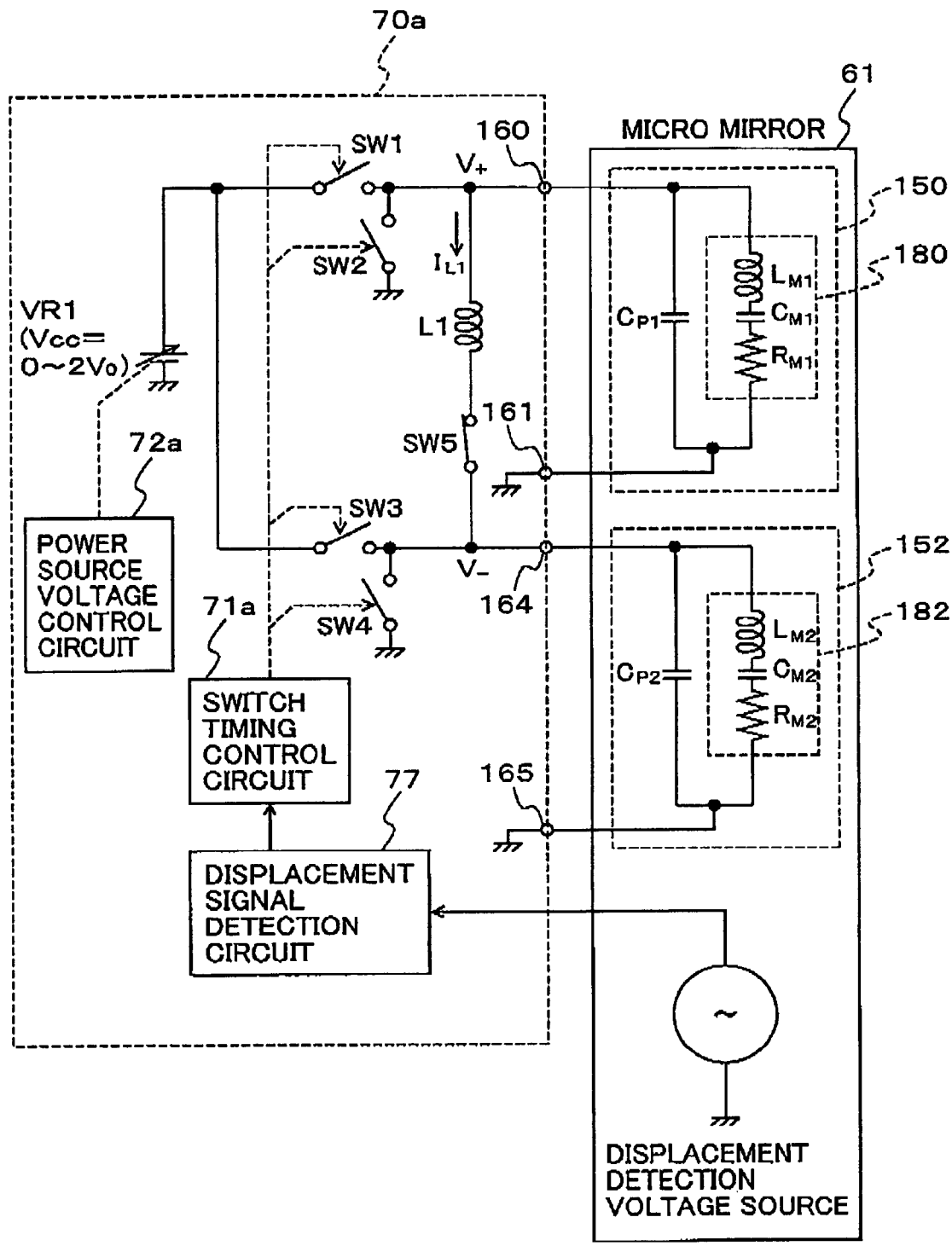
FIG. 10 is a view showing the constitution of the horizontal scanning optical scanner and another horizontal scanning drive circuit in the first embodiment.

First of all, as shown in FIG. 9 and FIG. 10, a displacement signal detection circuit 77 for detecting the displacement state of the horizontal scanning optical scanner 61 is mounted in the horizontal scanning drive circuit 70*a*. Based on a result detected by the displacement signal detection circuit 77, the switch timing control circuit 71*a* determines timings at which the voltage levels of the sinusoidal voltages of the driving terminal 160 and the driving terminal 164 assume approximately maximum values or approximately minimum values, and controls the switches SW1 to SW4 based on the determination.

Here, the horizontal scanning optical scanner 61 is configured such that, as described above, the displacement similar to the displacement of the first beam portion 140 is generated in the second beam portion 141, and the displacement is converted into the voltage by the third piezoelectric element 151 and the fourth piezoelectric element 153. Here, the third piezoelectric element 151 and the fourth piezoelectric element 153 correspond to a displacement detection voltage source in FIG. 10.

Further, the displacement signal detection circuit 77 is a circuit for detecting a displacement generated in the reflection mirror 120 in response to signals outputted from the third piezoelectric element 151 and the fourth piezoelectric element 153 (hereinafter, referred to as "output signals"), and an operation frequency (displacement frequency) and an amplitude (displacement range) of the reflection mirror 120 are detected in response to the signals. Here, the oscillation frequency of the reflection mirror 120 is detected based on a frequency of the sinusoidal voltage of the output signal, and the amplitude of the reflection mirror 120 is detected based on an amplitude level of the sinusoidal voltage of the output signal. In this manner, the displacement signal detection circuit 77 performs a function of a reflection mirror displacement detection means.

Further, the switch timing control circuit 71*a* determines the timings at which the voltage levels of the sinusoidal voltages assume the approximately maximum values or the approximately minimum values at the driving terminal 160 and the driving terminal 164 based on the amplitude detected by the displacement signal detection circuit 77, and the switch timing control circuit 71*a* alternately brings the switches SW1 and SW4 and the switches SW2 and SW3 in a short-circuit state for a predetermined period.

In this manner, the horizontal scanning drive circuit 70*a* controls the switches SW1 to SW4 at timings at which the voltage levels of the sinusoidal voltages at the driving terminal 160 and the driving terminal 164 assume approximately maximum values or approximately minimum values and hence, it is possible to control the switches SW1 to SW4 at suitable timings. Further, the voltage levels of the sinusoidal voltages of the driving terminal 160 and the driving terminal 164 are detected using the third piezoelectric element 151 and the fourth piezoelectric element 153 mounted on the horizontal scanning optical scanner 61 and hence, it is unnecessary to provide an extra circuit.

Further, the switch timing control circuit 71*a* functions as a malfunction detection portion for detecting an operational malfunction of the horizontal scanning optical scanner 61 based on the amplitude or the operation frequency detected by the displacement signal detection circuit 77. Here, when the operational malfunction of the horizontal scanning optical scanner 61 is detected by the switch timing control circuit 71a and a malfunction detection signal is outputted to the signal processing circuit 21 from the switch timing control circuit 71a, the signal processing circuit 21 functions as a control part which stops a display operation. Stopping of the display operation is performed by stopping an output of the optical flux from the light source part 30 or the like. Further, as the operational malfunction of the horizontal scanning optical scanner 61, an operational malfunction which occurs when the driving terminal voltage of the horizontal scanning optical scanner 61 assumes an abnormal voltage, an operational malfunction which occurs when the driving terminal voltage assumes an abnormal frequency or the like may be considered.

In this manner, since the display operation is stopped when the operational malfunction of the horizontal scanning optical scanner 61 is detected, it is possible to provide the retina scanning display device with increased safety.

Second Embodiment

In the above-mentioned first embodiment, the resonance circuit is constituted by providing the coil between the first piezoelectric element 150 and the second piezoelectric element 152. However, in this embodiment, the resonance circuit is constituted for each piezoelectric element 150, 152. Here, this embodiment is characterized by changing the constitution of the horizontal scanning drive circuit 70a in the first embodiment, and other constitutions are substantially the same as the corresponding constitutions of the first embodiment and hence, the explanation of other constitutions is omitted.

Figure 11:
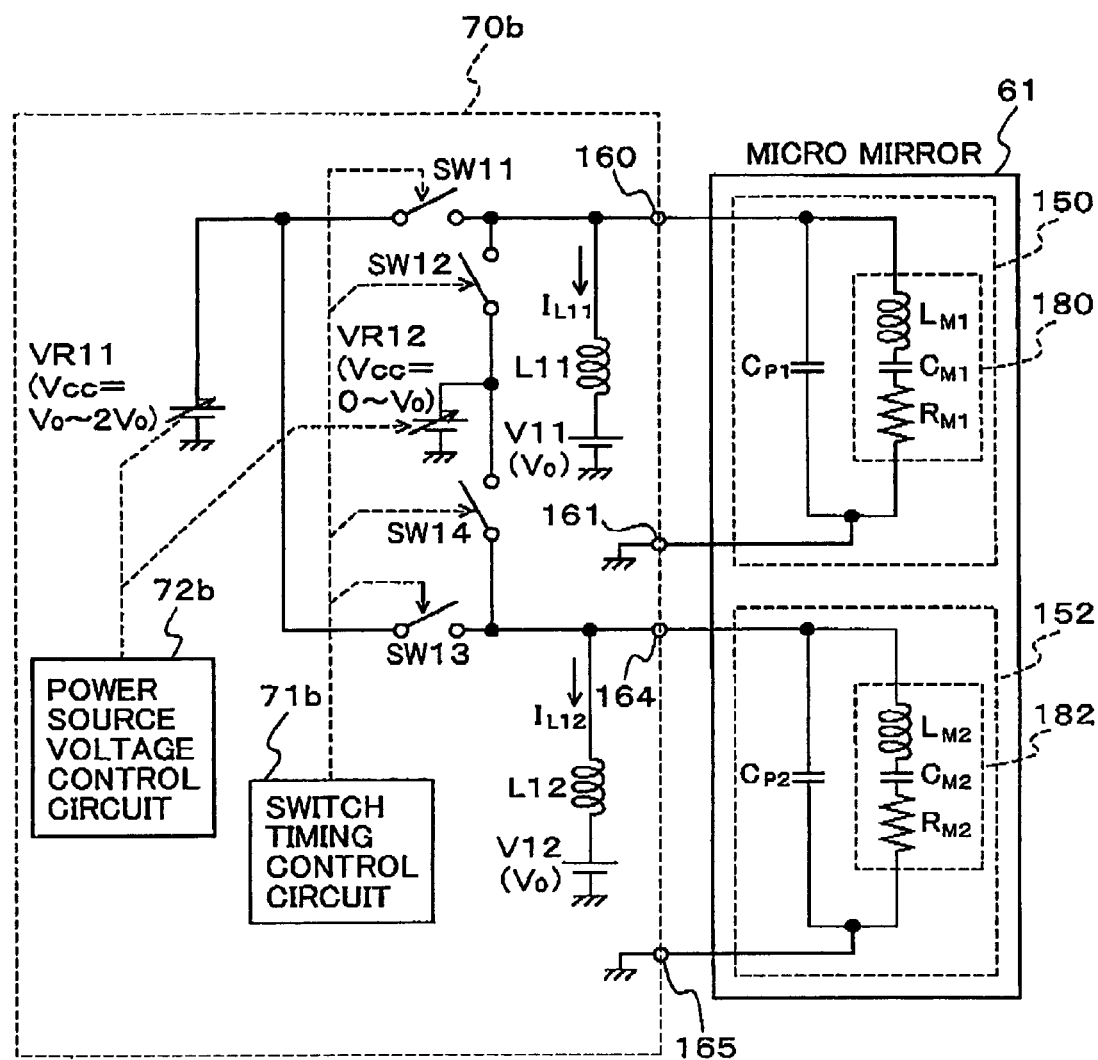
FIG. 11 is a view showing the constitution of a horizontal scanning optical scanner and a horizontal scanning drive circuit in the second embodiment.

Hereinafter, the horizontal scanning drive circuit 70b in this embodiment is specifically explained in conjunction with FIG. 11. FIG. 11 shows the constitution of the horizontal scanning drive circuit 70b.

As shown in FIG. 11, in the horizontal scanning drive circuit 70b, a coil L11 which constitutes a first inductor and a constant voltage source V11 (=Vo) are connected in series between the driving terminal 160 connected to the first piezoelectric element 150 and the ground and, in the same manner, a coil L12 which constitutes a second inductor and a constant voltage source V12 (=Vo) are connected in series between the driving terminal 164 connected to the second piezoelectric element 152 and the ground.

Here, in this embodiment, in the same manner as the first embodiment, the first piezoelectric element 150 can be regarded as a first capacitive load consisting of the capacitor $C_{P1}$, and the second piezoelectric element 152 can be regarded as a second capacitive load consisting of the capacitor $C_{P2}$.

Here, the resonance circuit is constituted of the first capacitive load and the coil L11, and the resonance circuit is constituted of the second capacitive load and the coil L12. In these resonance circuits, the constants of the coils L11 and L12 are determined so that the resonance frequencies of the resonance circuits become substantially equal to the operation frequency of the horizontal scanning optical scanner 61. As described above, the horizontal scanning optical scanner 61 is an electromechanical transducer device which includes the mechanical resonance system and hence, the resonance point of the resonance circuits becomes the operation frequency of the horizontal scanning optical scanner.

Here, the operation frequency f1 of the horizontal scanning optical scanner 61, as explained in the first embodiment, is expressed as follows:

$$f1=(2\pi)^{-1}(L_M \times C_M)^{-0.5} \tag{1}$$

Further, the resonance frequency f11 of the first resonance circuit and the resonance frequency f12 of the second resonance circuit are expressed as follows:

$$f11=(2\pi)^{-1}(L11 \times C_{P1})^{-0.5} \tag{5}$$

$$f12=(2\pi)^{-1}(L12 \times C_{P2})^{0.5} \tag{6}$$

Accordingly, the constants of the coils L11 and L12 are set such that the relationships f1≅f11, f1≅f12 are satisfied respectively.

Further, one end of a switch SW11 and one end of a switch SW12 are connected to the driving terminal 160 connected to the first piezoelectric element 150. Another end of the switch SW11 is connected to a variable voltage source VR11, while another end of the switch SW12 is connected to a variable voltage source VR12. When the switch SW11 is brought into a short-circuited state, the driving terminal 160 is connected to a variable voltage source VR11, while when the switch SW12 is brought into a short-circuited state, the driving terminal 160 is connected to the ground.

In the same manner, one end of a switch SW13 and one end of a switch SW14 are connected to the driving terminal 164 connected to the second piezoelectric element 152. Another end of the switch SW13 is connected to the variable voltage source VR11, while another end of the switch SW14 is connected to the variable voltage source VR12. When the switch SW13 is brought into a short-circuited state, the driving terminal 164 is connected to the variable voltage source VR11, while when the switch SW14 is brought into a short-circuited state, the driving terminal 164 is connected to the variable voltage source VR12. Here, an output of the variable voltage source VR11 is variable within a range from Vo to 2Vo(V), and an output of the variable voltage source VR12 is variable within a range from 0 to Vo, and the variable voltage source VR11 and the variable voltage source VR12 are controlled by a power source voltage control circuit 72b. Here, it is assumed that the variable voltage source VR11 is 2Vo(V) and the variable voltage source VR12 is 0(V). That is, the variable voltage sources VR11, VR12 are operated as constant voltage sources.

The switches SW11 to SW14 are operated by a switching timing control circuit 71b so that short-circuiting and opening of the switches are controlled. Here, the switches SW11 to SW14 are constituted of a MOS-PET or the like. Further, the control circuit is constituted of the variable voltage sources VR11, VR12, the switches SW1 to SW4 and the switch timing control circuit 71b.

Figure 12:
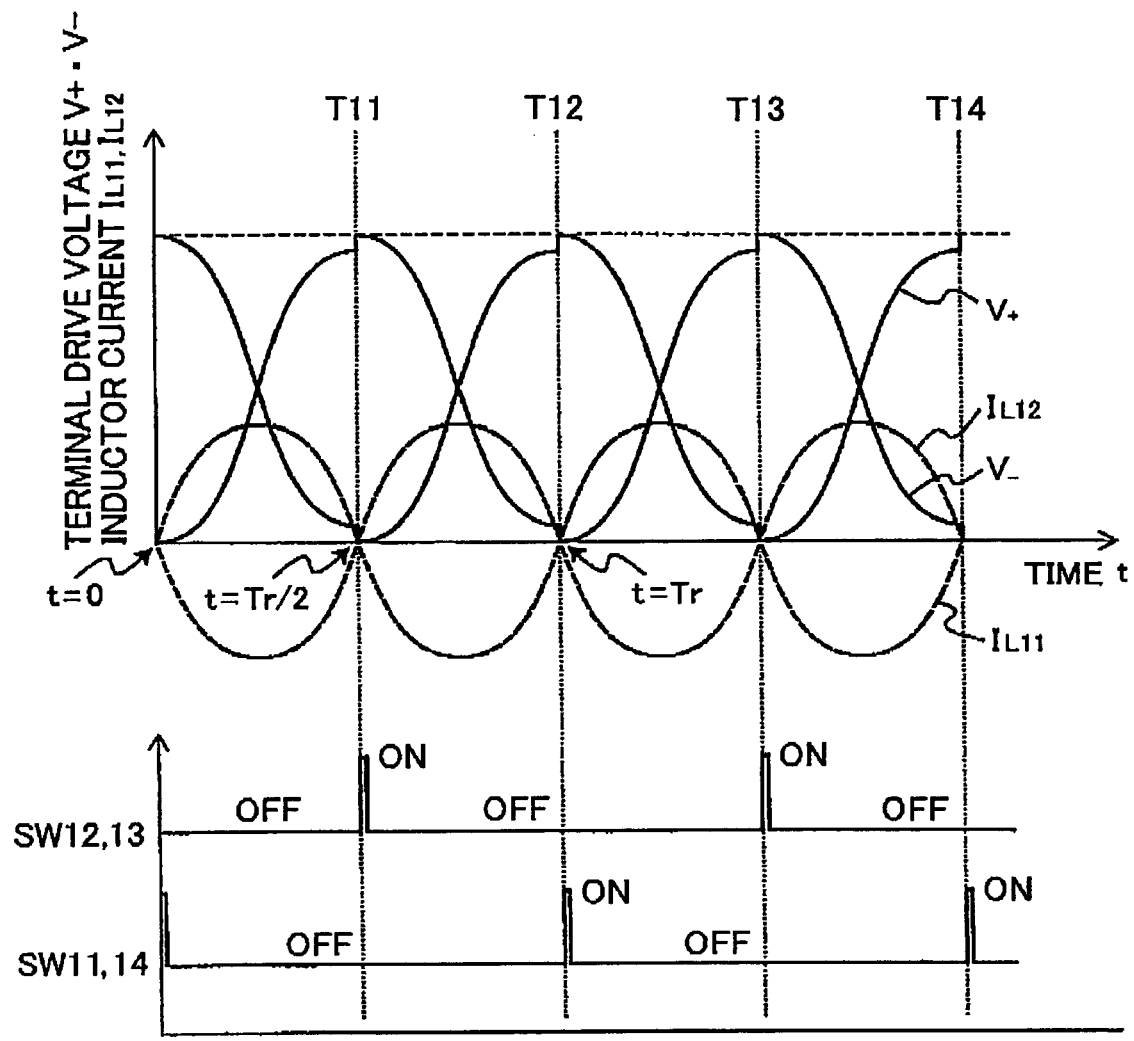
FIG. 12 is an explanatory view of a control of a switch in the horizontal scanning drive circuit shown in FIG. 11.

The manner of operation of the horizontal scanning drive circuit 70b which is constituted in the above-mentioned manner is specifically explained in conjunction with FIG. 12 and FIG. 13. FIG. 12 and FIG. 13 are views for explaining an output signal waveforms in the horizontal scanning drive circuit 70b and the control timing of SW1 to SW4 by the switch timing control circuit 71b.

As shown in FIG. 12, first of all, the switches SW11 and SW14 are brought into a short-circuited state by the switch timing control circuit 71b for a predetermined period (t=0 in FIG. 12). Accordingly, the driving terminal 160 is connected to the variable voltage source VR11 and hence, charge is charged (charge) to the capacitor $C_{P1}$ and, at the same time, the driving terminal 164 is connected to the variable voltage source VR13, and the charge of the capacitor $C_{P2}$ is discharged (discharge). As a result, the voltage of the capacitor $C_{P1}$ becomes 2Vo(V), while the voltage of the capacitor $C_{P2}$ becomes 0(V). Here, the variable voltage source VR11 is controlled to become 2Vo(V), while the voltage of the variable voltage source VR12 is controlled to become 0(V).

Thereafter, the charge which is charged to the capacitor $C_{P1}$ passes through the coil L12 and is charged to the capacitor $C_{P2}$ (0<t<T1). Accordingly, the voltage levels of the driving terminal 160 and the driving terminal 164 start changing as the sinusoidal voltages.

Here, due to the power consumption corresponding to a Q value of the resonance circuit (caused by loss attributed to inner resistances or the like of the coils L11, L12), as shown in FIG. 12, amplitude levels of the sinusoidal voltages of the driving terminal 160 and the driving terminal 164 are attenuated and hence, the voltage level of the driving terminal 160 does not arrive at 0(V), and the voltage level of the driving terminal 164 does not arrive at 2Vo(V).

Accordingly, in the switch timing control circuit 71b, when the voltage level of the sinusoidal voltage of the driving terminal 160 assumes the minimum value from the time when the switches SW11 and SW14 are brought into a short-circuited state for the predetermined period (or when the voltage level of the sinusoidal voltage of the driving terminal 164 assumes the maximum value), that is, after half cycles of the first and second resonance circuits (Tr/2) elapses, the switch timing control circuit 71b controls the switches SW12 and SW13 so as to bring these switches SW12 and SW13 into a short-circuited state for a predetermined period (t=T11). Here, the maximum value of the voltage level of the sinusoidal voltage may be an approximately maximum value, while the minimum value of the voltage level of the sinusoidal voltage may be an approximately minimum value.

In this manner, by bringing the switches SW12 and SW13 into a short-circuited state for the predetermined period, it is possible to change the voltage level of the driving terminal 160 from the minimum value to 0(V) and the voltage level of the driving terminal 164 from the maximum value to 2Vo(v). Accordingly, with charging or discharging of a slight amount of charge, it is possible to correct the attenuation of the sinusoidal voltages of the driving terminal 160 and the driving terminal 164.

In the same manner, hereinafter, the switch timing control circuit 71b, for every half cycle (Tr/2) of the resonance circuits, alternately bring the switches SW11 and SW14 and the switches SW12 and SW13 into a short-circuited state (t=T12, T13, T14) so as to correct the attenuation of the sinusoidal voltages of the driving terminal 160 and the driving terminal 164.

Here, in this embodiment, to facilitate the explanation, the switches SW11 and SW14 and the switches SW12 and SW13 are alternatively brought into a short-circuited state for every half cycles (Tr/2) of the first and second resonance circuits. However, when the power consumption corresponding to the value Q of the resonance circuits is small, the control of the switches may be performed in accordance with the attenuation of the sinusoidal voltage for, for example, every 10 cycles or every 20 cycles of the resonance circuit.

In the horizontal scanning drive circuit 70b, a main factor of the loss is a resistance loss attributed to the inductor and, assuming Q values of the first and second resonance circuits as Q11, Q12 respectively, the power consumption P2' of the horizontal scanning drive circuit 70a can be expressed as follows.

$$P2'=(2\pi f11 \times C_{P1} \times Vo)/Q11+(2\pi f12 \times C_{P2} \times Vo)/Q12 \quad (7)$$

Here, assuming the resonance frequencies as f11, f12=30 kHz, the capacitive values as $C_{P1}$, $C_{P2}$=1 nF, the voltage as Vo=15V, and the 0 factors as Q11, Q12=50, the power consumption P2' is expressed as: P2'=1.70 mW.

In this manner, according to this embodiment, it is possible to avoid the power consumption generated by a reactive force attributed to charging/discharging of the capacitive load and hence, it is sufficient to compensate for only the net power consumption. Furthermore, a linear amplifier becomes unnecessary and hence, the horizontal scanning drive circuit 70b can be constituted of only a digital circuit and a DC voltage source.

Further, in the horizontal scanning drive circuit 70b, at the time of starting the horizontal scanning optical scanner 61, as shown in FIG. 13, it is possible to gradually elevate the output voltage level of the variable voltage source VR11 from Vo(V) to 2Vo(V) and, at the same time, it is also possible to allow the output voltage level of the variable voltage source VR12 to gradually fall from Vo(V) to 0(V). Accordingly, it is possible to suppress electric currents which flow in the first piezoelectric element 150 and the second piezoelectric element 152. That is, it is possible to gradually perform charging/discharging of a charge to/from the capacitors $C_{P1}$, $C_{P2}$ and, as a result, it is possible to suppress the generation of noises or the like. Further, it is possible to prevent a malfunction of the horizontal scanning optical scanner 61 attributed to an overcurrent.

Here, in the same manner as the first embodiment, it is needless to say that, in the horizontal scanning drive circuit 70b, by providing the correction capacitors to the capacitors $C_{P1}$, $C_{P2}$ in series or in parallel, it is possible to adjust the resonance frequency.

Third Embodiment

In the above-mentioned first embodiment and the second embodiment, the switches are controlled so as to connect the voltage source or the ground to the first and second piezoelectric elements. In this embodiment, however, the constant power source is operated for a predetermined period. In this embodiment, the resonance circuit is constituted for each piezoelectric element 150, 152. Here, this embodiment is constituted by changing the constitution of the horizontal scanning drive circuit 70a in the first embodiment, and other constitutions are substantially equal to the corresponding constitutions of the first embodiment and hence, the explanation of other constitutions is omitted.

Figure 14:
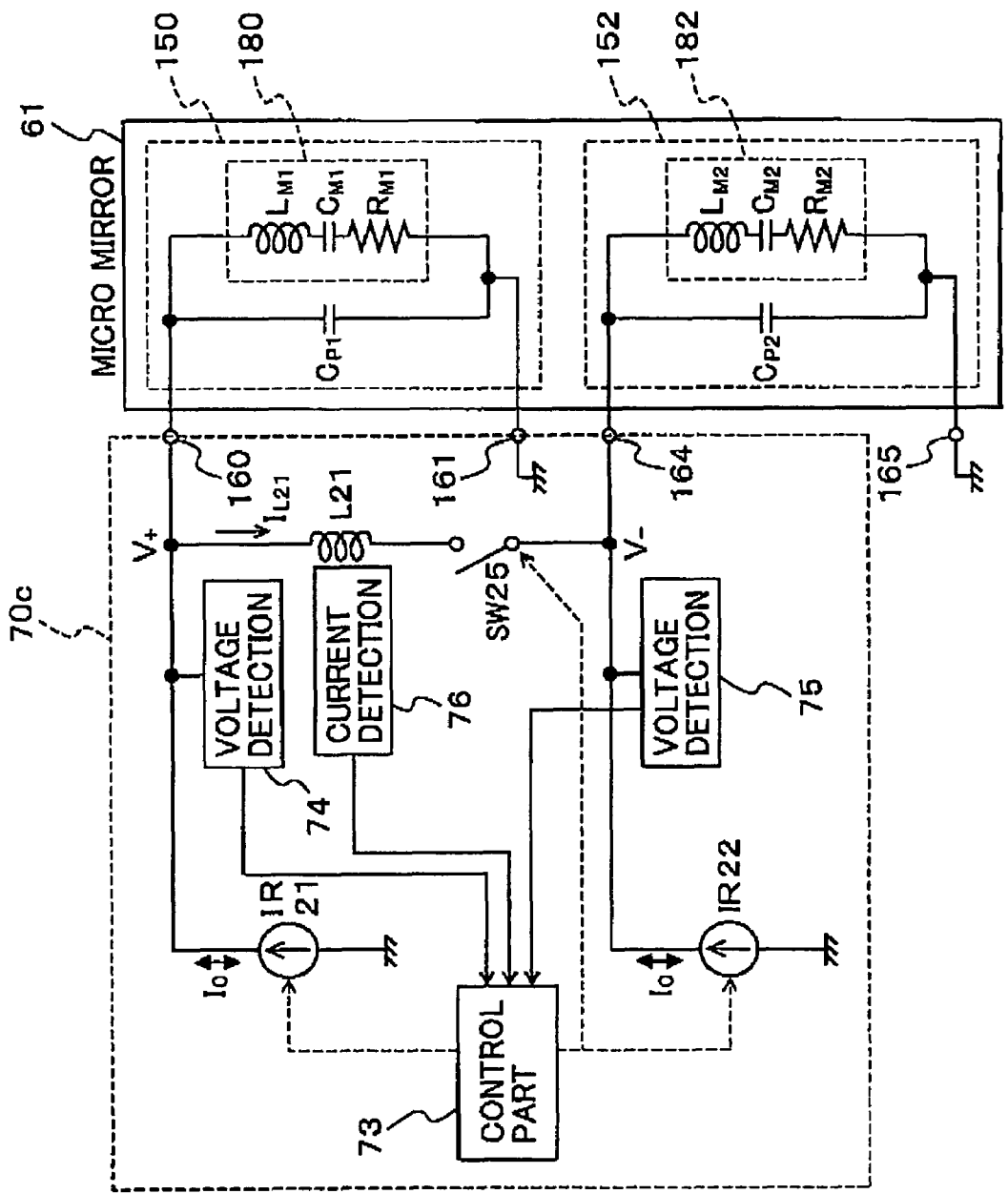
FIG. 14 is a view showing the constitution of a horizontal scanning optical scanner and a horizontal scanning drive circuit in the third embodiment.

Hereinafter, the horizontal scanning drive circuit 70c in this embodiment is specifically explained in conjunction with the drawings. FIG. 14 is a view showing the constitution of the horizontal scanning drive circuit 70c.

In the horizontal scanning drive circuit 70c, as shown in FIG. 14, a switch SW25 and a coil L21 are connected in series between the driving terminal 160 connected to the first piezoelectric element 150 and the driving terminal 164 connected to the second piezoelectric element 152. By bringing the switch SW25 into a short-circuited state, the driving terminal 161 and the driving terminal 164 are connected with each other via the coil L21.

Here, in this embodiment, in the same manner as the first embodiment, the first piezoelectric element 150 is assumed as a first capacitive load formed of the capacitor $C_{P1}$, and the second piezoelectric element 152 is assumed as a second capacitive load formed of the capacitor $C_{P2}$.

Here, the resonance circuit is constituted of the first capacitive load, the second capacitive load and the coil L21. A constant of the coil L21 is determined so that the resonance frequency of the resonance circuit becomes substantially equal to the operation frequency of the horizontal scanning optical scanner 61. As described above, the horizontal scanning optical scanner 61 is an electromechanical transducer device which includes the mechanical resonance system and hence, the resonance point becomes the operation frequency of the horizontal scanning optical scanner 61.

Further, the driving terminal 160 is connected to a first constant current source IR21, and when this first constant current source IR21 is brought into an operation state, a current Io is outputted from or inputted to the first constant current source IR21. In the same manner, the driving terminal 164 is connected to a second constant current source IR22, and when this second constant current source IR22 is brought into an operation state, a current Io is outputted to or inputted from the second constant power source IR22.

Here, the constant current sources IR21 and IR 22 are controlled to assume either of an operation state or a non-operation state by the control part 73 which constitutes a control circuit. Further, the control part 73 controls a short-circuited state or an opening state of the switch SW25 and, when the constant current sources IR21 and IR22 are operated, brings the switch SW25 into a disconnection state so as to prevent unnecessary current from flowing in the coil.

Further, the horizontal scanning drive circuit 70c includes a first voltage detection part 74 for detecting a voltage of the driving terminal 160, a second voltage detection part 75 for detecting a voltage of the driving terminal 164, and a current detection part 76 for detecting a current which flows in the coil L21. The control part 73 inputs information on the voltage or the current detected by these detection parts. Then, the control part 73 controls the switch SW25 or the constant current sources IR21 and IR22 corresponding to the inputted information. In this embodiment, although the current detection part 76 is constituted of a Hall element or the like, the current detection part 76 is not limited to such a constitution.

Figure 15:
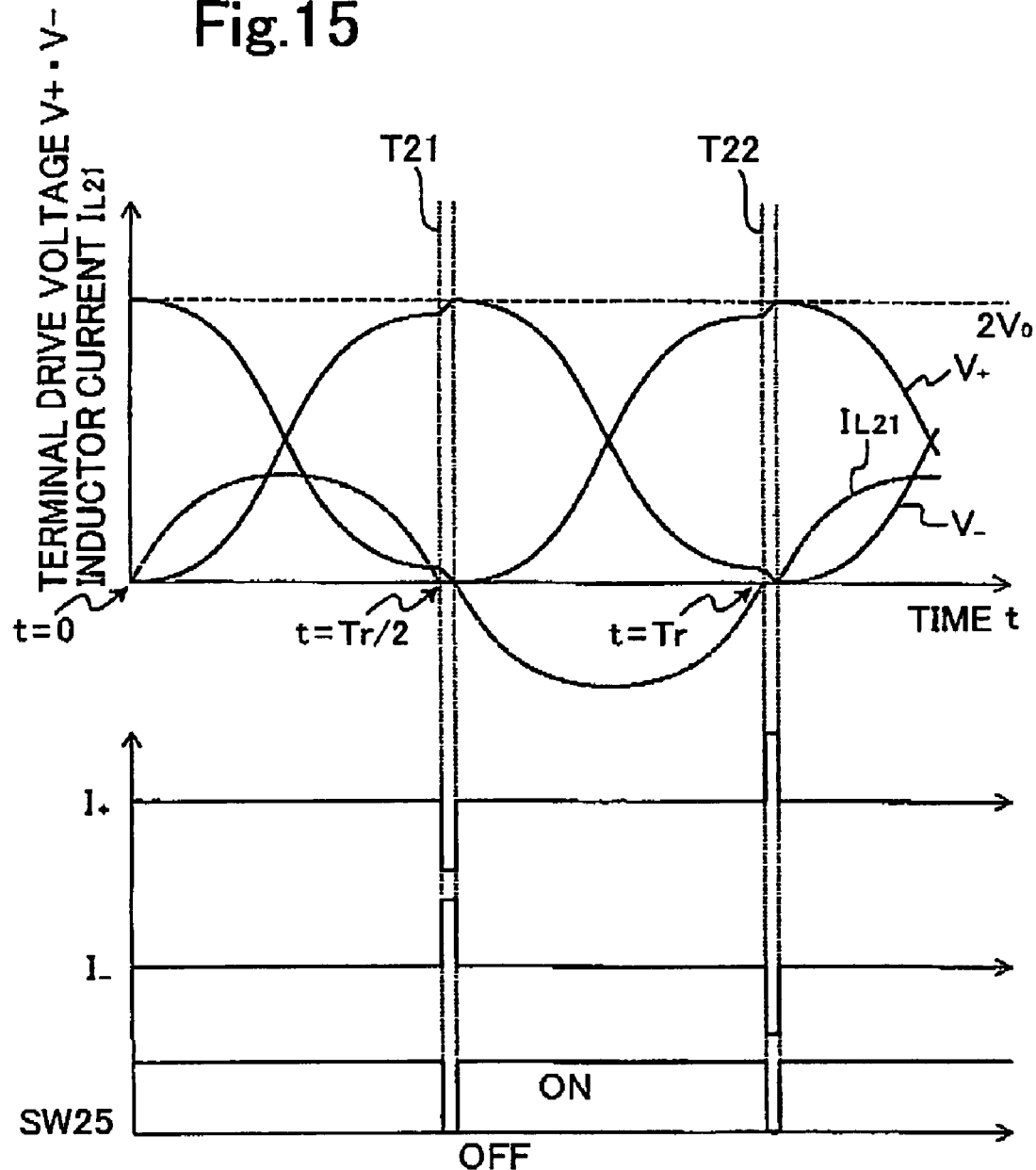
FIG. 15 is an explanatory view of a control of a switch in the horizontal scanning drive circuit shown in FIG. 14.
Figure 16:
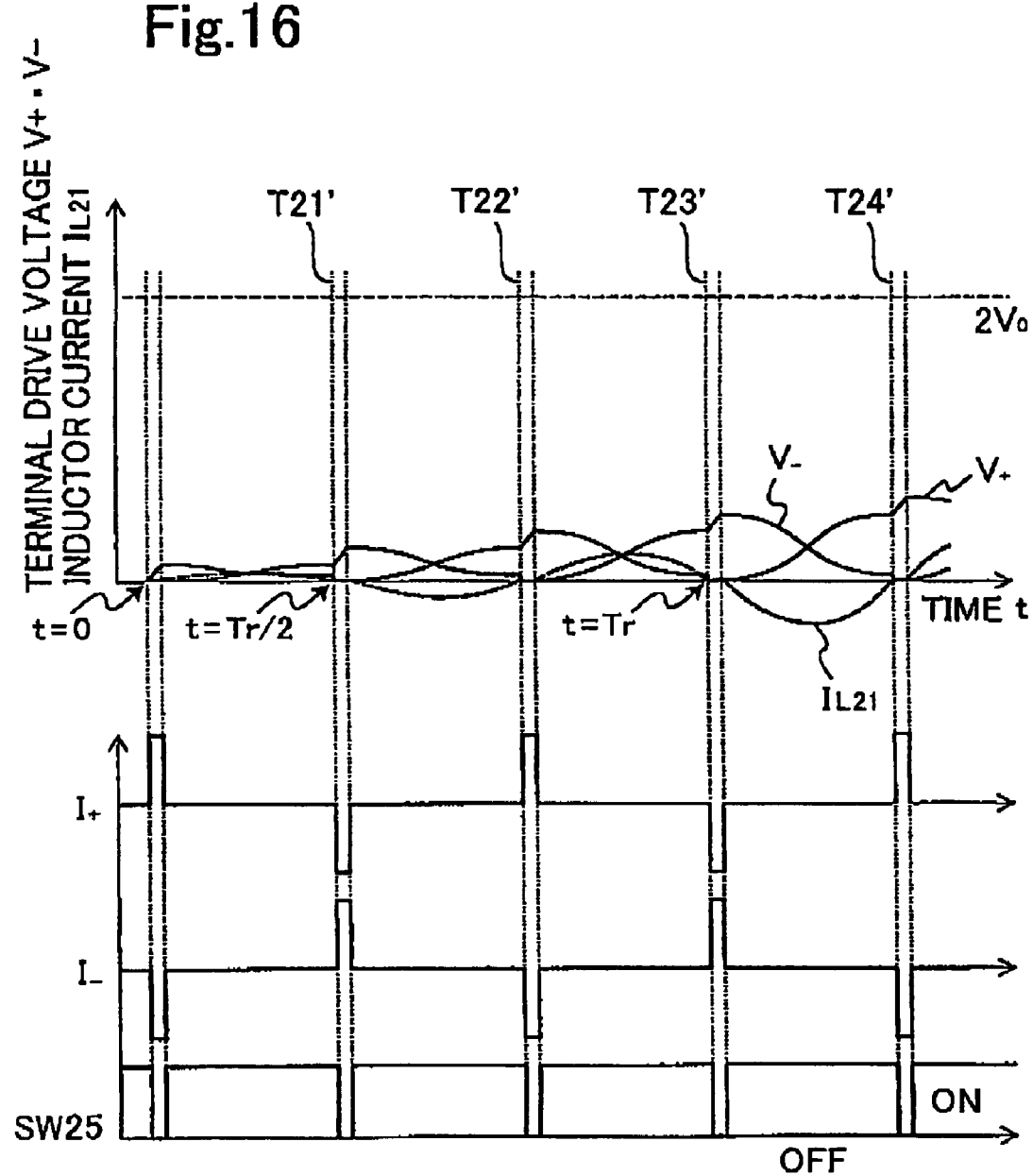
FIG. 16 is an explanatory view of a control of a switch in the horizontal scanning drive circuit shown in FIG. 14.
Figure 17:
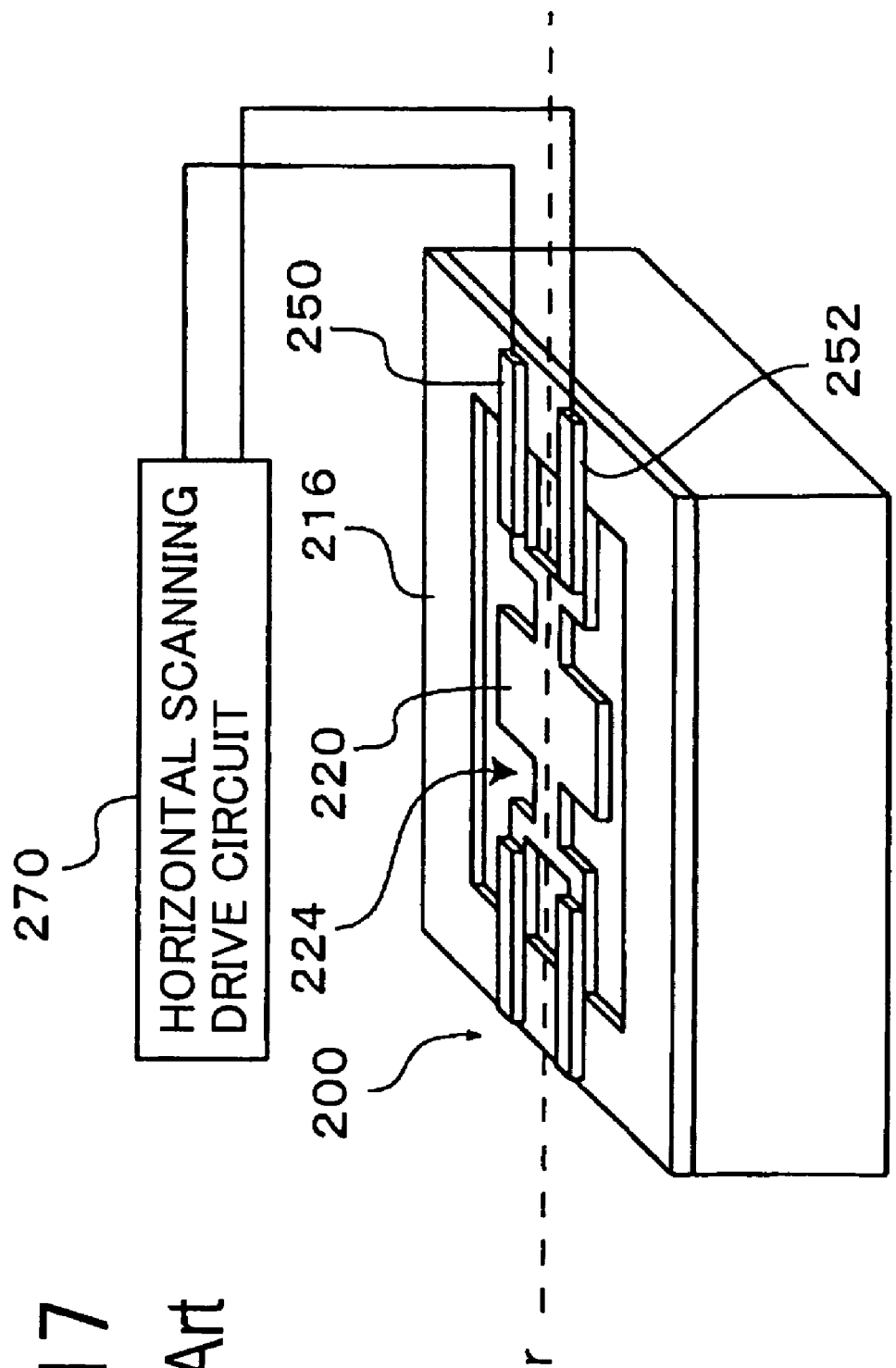
FIG. 17 is a view showing the connection between a horizontal scanning optical scanner and a horizontal scanning drive circuit of a prior art.

The operation of the horizontal scanning drive circuit 70c having the above-mentioned constitution is specifically explained in conjunction with the drawings. FIG. 15 and FIG. 16 are views for explaining an output signal waveform of the horizontal scanning drive circuit 70a and the control timing by the control part 73. Here, in FIG. 15, to facilitate the explanation, the explanation is made assuming that the voltage of the driving terminal 160 is 2Vo(V) and the voltage of the driving terminal 164 is 0(V) at the time point of t=0. Further, at this time, it is assumed that the current does not flow in the L21 (the switch SW which has been in a disconnection state is brought into a short-circuited state at t=0).

As shown in FIG. 15, the charge which is charged to the capacitor $C_{P1}$ passes through the coil 121 and is charged to the second capacitive load (0<t<T21). Accordingly, the voltage levels of the driving terminal 160 and the driving terminal 164 start changing as the sinusoidal voltages.

Here, due to the power consumption corresponding to a Q value of the resonance circuit (mainly, resistance loss of the coil L21), as shown in FIG. 15, amplitude levels of the sinusoidal voltages of the driving terminal 160 and the driving terminal 164 are attenuated and hence, the voltage level of the driving terminal 160 does not arrive at 0(V), and the voltage level of the driving terminal 164 does not arrive at 2Vo(V).

Here, the control part 73 inputs information on the current outputted from a current control part 76 and flowing in the coil L21. Upon detecting that the current flowing in the coil L21 becomes 0 A or approximately 0 A, the control part 73 brings the switch SW25 into an opening state and, at the same time, brings the constant current sources IR21 and IR22 into an operation state. Here, the current which flows in the coil L21 becomes 0 A or approximately 0 A for every halt cycle of the resonance circuit.

Thereafter, the control part 73 determines whether or not the voltage level of the driving terminal 160 becomes 0(v) and the voltage level of the driving terminal 164 becomes 2Vo(V) based on information from a first voltage detection part 74 and a second voltage detection part 7S. As a result of the determination, when it is determined that the voltage level of the driving terminal 160 becomes 0(V) and the voltage level of the driving terminal 164 becomes 2Vo(V), the control part 73 brings the switch SW25 into a short-circuited state and, at the same time, brings the constant current sources IR21 and IR22 into a non-operation state. In this manner, the current is allowed to flow from the constant current sources XR21, IR22 for a predetermined period, and a slight charge is charged or discharged and hence, it is possible to correct the attenuated sinusoidal voltage.

Hereinafter, in the same manner as the first and second embodiments, the control part 73 alternately inverts the directions of the output currents Io of the constant current sources IR21, IR22 for every half cycle (Tr/2) of the resonance circuits so as to correct the attenuation of the sinusoidal voltages of the driving terminal 160 and the driving terminal 164.

Here, in this embodiment, to facilitate the explanation, the constant current sources IR21, IR22 are brought into an operation state for every half cycle (Tr/2) of the first and second resonance circuits. However, when the power consumption corresponding to the Q values of the resonance circuits (mainly, resistance loss of the coil) is small, the control of the constant current sources IR21, IR22 may be performed in conformity with the attenuation of the sinusoidal voltage for, for example, every 10 cycles or every 20 cycles of the resonance circuit.

In this manner, according to this embodiment, it is possible to prevent the power consumption generated by a reactive power attributed to charging/discharging of a charge to/from the capacitive load. Further, a linear amplifier becomes unnecessary and hence, the horizontal scanning drive circuit 70c can be constituted of only a digital circuit and the constant current sources.

In starting the driving of the horizontal scanning optical scanner 61 also, the horizontal scanning drive circuit 70c performs a control to bring the constant current sources IR21, IR22 into an operation state for a predetermined period for every half cycle (Tr/2) of the resonance circuit. Accordingly, as shown in FIG. 16, the amplitude levels of the sinusoidal voltages which change as the voltages of the driving terminals 160 and 164 are gradually increased. Here, to quickly shift the horizontal scanning optical scanner 61 to a steady operation state, the horizontal scanning drive circuit 70c performs a control of prolonging a period while the constant current sources IR21, R22 are in an operation state at starting the driving.

Further, in this embodiment, the constitution which uses the constant current sources IR21, IR22 is explained. However, variable current sources may be used as the current sources IR21, IR22. By changing the current values of the current sources IR21, IR22, it is also possible to allow a current conforming to a state of the horizontal scanning optical scanner 61 to flow.

Further, in starting the driving of the horizontal scanning optical scanner 61, a time until the operation of the horizontal scanning optical scanner 61 is stabilized may be shortened by prolonging a period for driving the constant current sources IR21, IR22.

Heretofore, although the several embodiments of the present invention have been explained in detail in conjunction with the drawings, these embodiments are provided for an exemplary purpose, and the present invention can be exercised in other modes to which various modifications and improvements are applied based on knowledge of those who are skilled in the art including the modes described in the Disclosure of the Invention. For example, it is needless to say that the driving circuit to which the present invention is applied is also used as a driving circuit scanning a luminous flux inside a laser printer.

The present invention is applicable to the driving circuit for driving a capacitive electromechanical transducer device operated in response to two-phase sinusoidal signals having phases opposite from each other.

What is claimed is:

1. A drive circuit for driving a capacitive electromechanical transducer device operated in response to two-phase sinusoidal signals having phases opposite to each other, the driver circuit comprising an inductor forming a resonance circuit having a resonance frequency substantially equal to an operation frequency of the electromechanical transducer device together with the electromechanical transducer device;
    wherein the electromechanical transducer device is constituted of at least two capacitive electromechanical transducer parts consisting of a first capacitive electromechanical transducer part and a second electromechanical transducer part, and
    the inductor is provided to connect a drive terminal of the first electromechanical transducer part and a drive terminal of the second electromechanical transducer part.

2. A drive circuit according to claim 1 further comprising a correction capacitor arranged in parallel to or in series with the first electromechanical transducer part and/or the second electromechanical transducer part respectively.

3. A drive circuit according to claim 1 further comprising a control circuit performing a charge control and/or a discharge control for setting the drive terminal voltage to a predetermined voltage at timing that a drive terminal voltage level of the electromechanical transducer part constituting the resonance circuit assumes an approximately maximum value or an approximately minimum value or at timing that an electric current flowing into the inductor assumes approximately zero.

4. A drive circuit according to claim 3, wherein the control circuit includes a voltage source, a switch and a timing control part, the switch is arranged between the resonance circuit and the voltage source and/or between the resonance circuit and a ground, and
    the timing control part controls the switch at timing that the drive terminal voltage level of the electromechanical transducer part constituting the resonance circuit assumes the approximately maximum value or the approximately minimum value or at timing that the electric current flowing into the inductor assumes approximately zero.

5. A drive circuit according to claim 4, wherein the control circuit gradually elevates and sets an output voltage level of the voltage source to a fixed value at the time of starting the electromechanical transducer device.

6. A drive circuit according to claim 3, wherein the control circuit includes a current source and a timing control part,
    the current source is connected to the resonance circuit, and
    the timing control part operates the current source at timing that the drive terminal voltage level of the electromechanical transducer part constituting the resonance circuit assumes an approximately maximum value or an approximately minimum value or at timing that the electric current flowing into the inductor assumes approximately zero.

7. A drive circuit according to claim 3, wherein the drive circuit includes a current detection part for detecting an electric current flowing into the inductor, and
    the current detection part detects the timing that the electric current flowing into the inductor assumes approximately zero.

8. A drive circuit according to claim 3, wherein the drive circuit includes a displacement detection part for detecting a displacement of the electromechanical transducer device, and
    the displacement detection part detects the timing that the drive terminal voltage level of the electromechanical transducer part constituting the resonance circuit assumes approximately maximum value or an approximately minimum value.

9. A drive circuit according to claim 1, wherein the electromechanical transducer device includes a mechanical resonance system which resonates at the predetermined frequency by the first electromechanical transducer part and the second electromechanical transducer part.

10. A drive circuit according to claim 1, wherein the electromechanical transducer device is a scanning mirror for scanning an optical flux.

11. A retina scanning display device which includes the drive circuit according to claim 10.

12. A retina scanning display device according to claim 11, wherein the retina scanning display device further includes:
    an abnormality detection part for detecting an operation abnormality in the electromechanical transducer device; and
    a control part which controls a display operation when the abnormality is detected by the abnormality detection part.

13. A retina scanning display device according to claim 11, wherein the retina scanning display device uses the electromechanical transducer device as a scanning mirror for main scanning and/or sub scanning.

14. A drive circuit for driving a capacitive electromechanical transducer device operated in response to two-phase sinusoidal signals having phases opposite to each other, the driver circuit comprising an inductor forming a resonance circuit having a resonance frequency substantially equal to an operation frequency of the electromechanical transducer device together with the electromechanical transducer device;
    wherein the electromechanical transducer device is constituted of at least two capacitive electromechanical transducer parts consisting of a first electromechanical transducer part and a second electromechanical transducer part, and
    the inductor is constituted of at least a first inductor and a second inductor, the first inductor forms the resonance circuit with the first electromechanical transducer part, and the second inductor forms the resonance circuit with the second electromechanical transducer part.

15. A drive circuit according to claim 14, wherein the electromechanical transducer device is a scanning mirror for scanning an optical flux.

16. A retina scanning display device which includes the drive circuit according to claim 15.

17. A retina scanning display device according to claim 16, wherein the retina scanning display device further includes:
    an abnormality detection part for detecting an operation abnormality in the electromechanical transducer device; and
    a control part which controls a display operation when the abnormality is detected by the abnormality detection part.

18. A retina scanning display device according to claim 16, wherein the retina scanning display device uses the electromechanical transducer device as a scanning mirror for main scanning and/or sub scanning.

* * * * *